US012636299B2

(12) United States Patent
Urban et al.

(10) Patent No.: US 12,636,299 B2
(45) Date of Patent: May 26, 2026

(54) TERPENOID DERIVATIVES, PHARMACEUTICAL PREPARATIONS CONTAINING THESE DERIVATIVES AND THEIR USE IN NEUROPROTECTION

(71) Applicant: UNIVERZITA PALACKEHO V OLOMOUCI, Olomouc (CZ)

(72) Inventors: Milan Urban, Prague (CZ); Gabriel Gonzalez, Vrbátky (CZ); Jirí Hodon, Bohuŏvice (CZ); Miroslav Strnad, Olomouc (CZ)

(73) Assignee: UNIVERZITA PALACKEHO V OLOMOUCI, Olomouc (CZ)

( * ) Notice: Subject to any disclaimer, the term of this patent is extended or adjusted under 35 U.S.C. 154(b) by 413 days.

(21) Appl. No.: 18/036,564

(22) PCT Filed: Dec. 3, 2021

(86) PCT No.: PCT/CZ2021/050146
§ 371 (c)(1),
(2) Date: May 11, 2023

(87) PCT Pub. No.: WO2022/117133
PCT Pub. Date: Jun. 9, 2022

(65) Prior Publication Data

US 2023/0414645 A1 Dec. 28, 2023

(30) Foreign Application Priority Data

Dec. 4, 2020 (CZ) ................................ CZ2020-651

(51) Int. Cl.
*A61K 31/7056* (2006.01)
*A61K 31/341* (2006.01)
*A61K 31/4409* (2006.01)
*A61P 25/28* (2006.01)

(52) U.S. Cl.
CPC ........ *A61K 31/7056* (2013.01); *A61K 31/341* (2013.01); *A61K 31/4409* (2013.01); *A61P 25/28* (2018.01)

(58) Field of Classification Search
CPC .. A61K 31/56; A61K 31/7056; A61K 31/341; A61K 31/4409; A61P 25/28
See application file for complete search history.

(56) References Cited

FOREIGN PATENT DOCUMENTS

CN 111 494 390 A 8/2020

OTHER PUBLICATIONS

Oxford English Dictionary, definition of "prophylaxis"; accessed Sep. 9, 2025. (Year: 2025).*
Oxford English Dictionary, definition of "prevent"; accessed Sep. 9, 2025. (Year: 2025).*
Minnesota Evidence-based Practice Center, "Interventions to Prevent Age-Related Cognitive Decline, Mild Cognitive Impairment, and Clinical Alzheimer's-Type Dementia" Mar. 2017. (Year: 2007).*
Mayo Clinic—Dementia, website updated Aug. 2, 2017; accessed via Internet Archive from Nov. 16, 2017. https://web.archive.org/web/20171116204052/https://www.mayoclinic.org/diseases-conditions/dementia/symptoms-causes/syc-20352013. (Year: 2017).*
Mayo Clinic—Parkinson's, website updated Jul. 7, 2015; accessed via Internet Archive from Dec. 22, 2017. https://web.archive.org/web/20171222030730/https://www.mayoclinic.org/diseases-conditions/parkinsons-disease/symptoms-causes/syc-20376055. (Year: 2015).*
Gonzalez, G.; et al. "Novel pentacyclic triterpenes exhibiting strong neuroprotective activity in SH-SY5Y cells in salsolinol- and glutamate-induced neurodegeneration models" European Journal of Medicinal Chemistry 2021, vol. 213, article 113168. (Year: 2021).*
Uzenkova, N. V.; et al. "Synthesis of 30-Amino Derivatives of Lupane Triterpenoids" Chemistry of Natural Compounds 2005, vol. 41, pp. 692-700. (Year: 2005).*
Sun, I.-C.; et al. "Anti-AIDS Agents. 34 Synthesis and Structure-Activity Relationships of Betulin Derivatives as Anti-HIV Agents", Journal of Medicinal Chemistry 1998, vol. 41, pp. 4648-4657. (Year: 1998).*
Ruszkowski, P.; et al. "Natural Triterpenoids and their Derivatives with Pharmacological Activity Against Neurodegenerative Disorders", Mini-Reviews in Organic Chemistry 2014, vol. 11, pp. 307-315. (Year: 2014).*
Alisky, J. M. "The coming problem of HIV-associated Alzheimer's disease", Medical Hypotheses 2007, vol. 69, pp. 1140-1143. (Year: 2007).*
Chrobak, E.; et al. "New 30-substituted derivatives of pentacyclic triterpenes: preparation, biological activity, and molecular docking study", Journal of Molecular Structure 2021, vol. 1226, 129394. (Year: 2021).*
Dang Zhao, et al.; "Synthesis of betulinic acid derivatives as entry inhibitors against HIV-1 and bevirimat-resistant HIV-1 variants"; Bioorganic & Medicinal Chemistry Letters, Jul. 3, 2012; 22(16):5190-5194.
International Search Report and Written Opinion for PCT Application No. PCT/CZ2021/1050146, mailed Mar. 21, 2022.
International Application Status Report generated Apr. 5, 2023.

* cited by examiner

*Primary Examiner* — Andrea Olson
*Assistant Examiner* — Benjamin M Brandsen
(74) *Attorney, Agent, or Firm* — Notaro, Michalos & Zaccaria P.C.

(57) ABSTRACT

Terpenoid derivatives for use in the medicinal applications and compositions containing these derivatives. This new generation of compounds possesses selective anti-neurodegenerative properties on neuronal cells and tissues and can be particularly used in the treatment and prophylaxis of neurodegenerative disease, particularly in the treatment and prophylaxis of Parkinson's and Huntington's disease.

7 Claims, 2 Drawing Sheets

TERPENOID DERIVATIVES, PHARMACEUTICAL PREPARATIONS CONTAINING THESE DERIVATIVES AND THEIR USE IN NEUROPROTECTION

FIELD OF ART

The invention relates to terpenoid derivatives, to their use in neuroprotection, and in particular for the treatment of Parkinson's and Huntington's disease and pharmaceutical compositions containing these derivatives.

BACKGROUND ART

Parkinson's disease (PD) in particular, with a 1% occurrence in populations over 60, is the most common motor-related and second most frequent neurodegenerative disease. Generally, PD is characterized by motor-associated symptoms such as bradykinesia (lack or slowness of movements), rigidity, resting tremor and postural instability, which are tightly linked with progressive and severe degeneration of dopaminergic neurons in Substantia nigra pars compacta in Basal ganglia. Appearance of early PD symptoms is linked with the degeneration and loss approx. 50-80% of DA neurons. Amongst many PD forms, idiopathic or sporadic PD predominates in rate of diagnosis. Additionally, there is not known specific cause for this form making the treatment of disease more problematic. On the other hand, several molecular hallmarks of PD such as proteasomal and autophagy-lysosomal dysfunction, stress of the endoplasmic reticulum, synaptopathy, mitochondrial dysfunction, oxidative stress, disruption of calcium homeostasis and neuroinflammation were identified. Currently PD is managed only by symptomatic treatment which is not effective in blockade or decrease of progression of disease (Rinne, Acta Neurol Scand. Suppl. 1983, 95, 19). Therefore, the drug development is currently focused on the promising disease-modifying therapy approaches. Specifically, several natural 19 or synthetic compounds or already approved CNS drugs showed encouraging neuroprotective activity in in vitro and in vivo models of neurodegenerative diseases (Schapira and Olanow, Jama 2004, 291, 358).

Pentacyclic triterpenes belong to the most abundant natural compounds, secondary metabolites that may be found in higher plants, fungi, algae, and marine animals. A large number of triterpenes have been isolated from natural sources and many of them are biologically active. There are many examples of cytotoxic, antibacterial, antifeedant, antiviral, anticariogenic, hepatoprotective, and cardioprotective triterpenic compounds and some of them reported to have neuroprotective activity such as tenuigenin38 or botulin (Hill and Connolly, Nat. Prod. Rep. 2018, 35, 1294; Zhang et al., Med. Res. Rev. 2015, 35, 1127). As long as our research group is focused on the preparation of triterpenoids, we have prepared hundreds of derivatives from betulinic acid and betulin, but many of them had inappropriate pharmacological properties such as low solubility in water. A series of triterpene conjugates were prepared during solubility improvement attempts but in some of them, coupling to another (polar) molecule caused significant decrease in their cytotoxicity (Hodon et al., Eur. J. Med. Chem. 2019, 182, 111653).

It is therefore an object of the present invention to provide a new generation of terpenoid derivatives which exhibit potent and selective anti-neurodegenerative properties on neuronal cells and tissues and can be advantageously used in the treatment and prophylaxis of neurodegenerative diseases, preferably Parkinson's and Huntington's disease. Some triterpene derivatives of this invention display strong neuroprotective effects in salsolinol (SAL)- and 3-nitropropionic acid (3NPA)-induced model of cell death. The terpenoid derivatives were also potent in decreasing of superoxide radical formation and caspase-3,7 activity on human neuron-like SH-SY5Y cells and glial A-172 cells and are thus usable for treatment of Parkinson's and Huntington's disease. Several of the terpenoid derivatives of general formula I have been prepared in the diploma thesis (Pavel Zoufalý, Studium click reakci u triterpenoidů obsahujicich propargylovou skupinu, UP v Olomouci, 2016), which was only focused on the synthesis of these compounds with expected antitumor activity (but this activity was not found in these compounds).

DISCLOSURE OF THE INVENTION

The object of this invention are terpenoid derivatives of the general formula I,

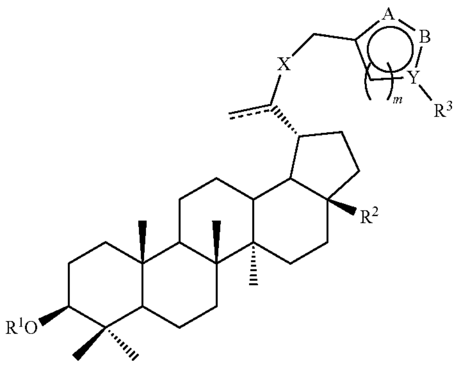

I wherein,

- ------ is single or double bond;
- X is independently selected from $CH_2NH$, $CH_2O$, C(O)NH, C(O)O
- A, B, and Y are independently on each occurrence selected from the group consisting of CH, C, N, NH, O, S;
- m=1, 2, 3;
- $R^1$ is independently selected from H—, $CH_3(CH_2)_nCO$— or $HOOC(CH_2)_nCO$— and n=0-5;
- $R^2$ is independently selected from —$CH_2OH$, —$CH_2O(CH_2)_nCH_3$, —$CH_2OC(O)(CH_2)_nCH_3$, —COOH, —$COO(CH_2)_nCH_3$ and $COO(CH_2)Ph$, wherein n=0-5;
- $R^3$ is independently on each occurrence H; C1-C6 alkyl; C6-C12 aryl, heteroaryl containing 5-8 atoms (with advantage 5 or 6 atoms) in the aromatic ring of that at least one is heteroatom selected from N, O, S; and monosaccharide molecule or its acetylated form (with advantage peracylated form);
- while $R^3$ is not present when Y is O or S;
- and their use as pharmaceutically acceptable salts
- for the use in the treatment and prophylaxis of neurodegenerative diseases The object of this invention are terpenoid derivatives of the general formula Ia,

I

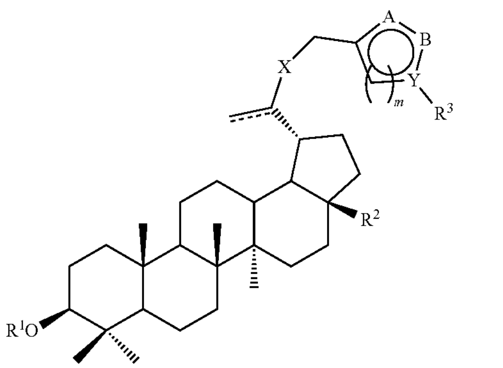

wherein,

----- is single or double bond;

X is independently selected from —$CH_2O$—, —C(O)NH—, —C(O)O—

A, B, and Y are independently on each occurrence selected from the group consisting of CH, C, N, NH, O, S;

m=1, 2, 3;

$R^1$ is independently selected from H—, $CH_3(CH_2)_n$CO— or $HOOC(CH_2)_n$CO— and n=0-5;

$R^2$ is independently selected from —$CH_2OH$, —$CH_2O(CH_2)_nCH_3$, —$CH_2OC(O)(CH_2)_nCH_3$, —COOH, —$COO(CH_2)_nCH_3$ and $COO(CH_2)Ph$, wherein n=0-5;

$R^3$ is independently on each occurrence H; C1-C6 alkyl; C6-C12 aryl; heteroaryl containing 5-8 atoms (with advantage 5 or 6 atoms) in the aromatic ring of that at least one is heteroatom selected from N, O, S; and monosaccharide molecule or its acetylated form (with advantage peracylated form); while $R^3$ is not present when Y is O or S;

provided that if X is C(O)NH or C(O)O, $R^1$ is $CH_3CO$—, $R^2$ is —$CH_2OC(O)CH_3$ or COOH, A=B=C=N and m=1; then $R^3$ is not phenyl, 4-aminophenyl, 4-thiocyanatophenyl, 2-carboxyphenyl, peracetylglucosyl, peracetylgalactosyl;

or

X is —$CH_2NH$—,

A, B, and Y are independently on each occurrence selected from the group consisting of CH, C, N, NH, O, S;

m=1, 2, 3;

$R^1$ is independently selected from H—, $CH_3(CH_2)_n$CO— or $HOOC(CH_2)_n$CO— and n=0-5;

$R^2$ is independently selected from —$CH_2OH$, —$CH_2O(CH_2)_nCH_3$, —$CH_2OC(O)(CH_2)_nCH_3$, —COOH, —$COO(CH_2)_nCH_3$ and $COO(CH_2)Ph$, wherein n=0-5;

$R^3$ is independently on each occurrence H; C1-C6 alkyl; heteroaryl containing 5-8 atoms (with advantage 5 or 6 atoms) in the aromatic ring of that at least one is heteroatom selected from N, O, S;

and monosaccharide molecule or its acetylated form (with advantage peracylated form); while $R^3$ is not present when Y is O or S;

and their use as pharmaceutically acceptable salts

In case there is an enantiomeric carbon in the molecule, this invention includes also racemates as well as optically active isomers and their mixtures.

In some embodiments, the compounds of this invention bear a substituent in the position $R^3$, that is selected from a group containing aryl or heteroaryl, with advantage selected from the group consisting of phenyl, triazolyl, pyridinyl, thiophenyl, imidazolyl, furyl, and pyrazinyl.

With advantage, the substituent in the position $R^3$ is heteroaryl or H or C1-C6 alkyl Especially when X is C(O)NH or C(O)O, $R^1$ is —$CH_2OC(O)CH_3$ or COOH, A=B=Y=N and m=1, then $R^3$ is with advantage H, heteroaryl, or C1-C6 alkyl In some embodiments, the compounds of the invention bear a substituent in the position $R^3$, that was selected from a group containing sugars, with advantage selected from the group consisting of glucose, galactose, mannose, rhamnose, lactose, ribose, arabinose, 2-deoxyglucose, 2-deoxygalactose, 2-deoxymannose and their peracetylated derivatives.

In especially advantageous embodiments, the R3 is selected from the group H, methyl, ethyl, propyl, isopropyl, phenyl, thiophenyl, pyridine-2-yl, pyridine-3-yl, pyridine-4-yl, imidazolyl, furyl, galactosyl, glucosyl, mannosyl, rhamnosyl, peracetylgalactosyl, peracetylglucosyl, peracetalrhamnosyl, peracetynmannosyl.

In some advantageous embodiments, one of the A, B, Y is a heteroatom (N, O, or S); and the other two substituents are CH (in case of A or B) or C (in case of Y). $R^3$ may be advantageously H or is not present or may be present in all mentioned meanings.

In another advantageous embodiments, two substituents from A, B, and Y are heteroatoms (N, O, or S); and remaining one substituent is CH (in case of A or B) or C (in case of Y). $R^3$ is advantageously hydrogen or is not present but it may have all possible mentioned meanings. In these embodiments it is advantageous when at least one heteroatom is nitrogen.

m is advantageously 1 or 2

The aromatic ring containing A, B, Y in the formula I and Ia is most advantageously the structure containing triazole, thiazole, pyrrole, thiofene, furane, imidazole, thiazole, oxazole, pyrrazole, pyridine, pyrimidine, pyrazine.

Individual compounds as shown in the examples represent individual preferred embodiments of the present invention.

Preferred compounds of the invention are the following compounds, wherein, X=$CH_2O$; $R^1$=C(O)$CH_3$, $R^2$=$CH_2OC(O)CH_3$.

Especially advantageous compounds are compounds selected from group: 30-1H-1,2,3-triazol-4-yl-methoxylup-20(29)-en-3,28-diol diacetate; 30-(1-methyl-1H-1,2,3-triazol-4-yl)-methoxylup-20(29)-en-3,28-diol diacetate; 30-(1-ethyl-1H-1,2,3-triazol-4-yl)-methoxylup-20(29)-en-3,28-diol diacetate; 30-(1-propyl-1H-1,2,3-triazol-4-yl)-methoxylup-20(29)-en-3,28-diol diacetate; 30-(1-furyl-1H-1,2,3-triazol-4-yl)-methoxylup-20(29)-en-3,28-diol diacetate; 30-(1-imidazolyl-1H-1,2,3-triazol-4-yl)-methoxylup-20(29)-en-3,28-diol diacetate; 30-(1-phenyl-1H-1,2,3-triazol-4-yl)-methoxylup-20(29)-en-3,28-diol diacetate; 30-(1-thiophenyl-1H-1,2,3-triazol-4-yl)-methoxylup-20(29)-en-3,28-diol diacetate; 30-(1-[pyridin-2-yl]-1H-1,2,3-triazol-4-yl)-methoxylup-20(29)-en-3,28-diol diacetate; 30-(1-[pyridin-3-yl]-1H-1,2,3-triazol-4-yl)-methoxylup-20(29)-en-3,28-diol diacetate; 30-(1-[pyridin-4-yl]-1H-1,2,3-triazol-4-yl)-methoxylup-20(29)-en-3,28-diol diacetate; 30-(1-[peracetyl glucos-1-yl]-1H-1,2,3-triazol-4-yl)-methoxylup-20(29)-en-3,28-diol diacetate; 30-(1-[peracetyl galactos-1-yl]-1H-1,2,3-triazol-4-yl)- methoxylup-20(29)-en-3,28-diol diacetate; 30-(1-[peracetyl mannos-1-yl]-1H-1,2,3-triazol-4-yl)-methoxylup-20(29)-en-3,28-diol diacetate; 30-(1-[peracetyl rhamnos-1-yl]-1H-1,2,3-triazol-4-yl)-methoxylup-20(29)-en-3,28-diol diacetate; 30-(1-[glucos-1-yl]-1H-1,2,3-triazol-4-yl)-methoxylup-20(29)-en-3,28-diol diacetate; 30-(1-[galactos-1-yl]-1H-1,2,3-triazol-4-yl)-methoxylup-20(29)-en-3,28-diol diacetate; 30-(1-[mannos-1-yl]-1H-1,2,3-triazol-4-yl)-methoxylup-20(29)-en-3,28-diol diacetate; 30-(1-[rhamnos-1-yl]-1H-1,2,3-triazol-4-yl)-methoxylup-20(29)-en-3,28-diol diacetate.

Preferred compounds of the invention are the following compounds, wherein X═$CH_2O$; $R^1$═H, $R^2$═$CH_2OH$ Especially advantageous compounds are compounds selected from group: 30-1H-1,2,3-Triazol-4-yl-methoxylup-20(29)-en-3,28-diol; 30-(1-methyl-1H-1,2,3-triazol-4-yl)-methoxylup-20(29)-en-3,28-diol; 30-(1-ethyl-1H-1,2,3-triazol-4-yl)-methoxylup-20(29)-en-3,28-diol; 30-(1-propyl-1H-1,2,3-triazol-4-yl)-methoxylup-20(29)-en-3,28-diol; 30-(1-furyl-1H-1,2,3-triazol-4-yl)-methoxylup-20(29)-en-3,28-diol; 30-(1-imidazolyl-1H-1,2,3-triazol-4-yl)-methoxylup-20(29)-en-3,28-diol; 30-(1-phenyl-1H-1,2,3-triazol-4-yl)-methoxylup-20(29)-en-3,28-diol; 30-(1-thiophenyl1H-1,2,3-triazol-4-yl)-methoxylup-20(29)-en-3,28-diol; 30-(1-[pyridin-2-yl]-1H-1,2,3-triazol-4-yl)-methoxylup-20(29)-en-3,28-diol; 30-(1-[pyridin-3-yl]-1H-1,2,3-triazol-4-yl)-methoxylup-20(29)-en-3,28-diol; 30-(1-[pyridin-4-yl]-1H-1,2,3-triazol-4-yl)-methoxylup-20(29)-en-3,28-diol; 30-(1-[peracetyl glucos-1-yl]-1H-1,2,3-triazol-4-yl)-methoxylup-20(29)-en-3,28-diol; 30-(1-[peracetyl galactos-1-yl]-1H-1,2,3-triazol-4-yl)-methoxylup-20(29)-en-3,28-diol; 30-(1-[peracetyl mannos-1-yl]-1H-1,2,3-triazol-4-yl)-methoxylup-30-(1-[peracetyl rhamnos-1-yl]-1H-1,2,3-triazol-4-yl)-methoxylup-20(29)-en-3,28-diol; 30-(1-[glucos-1-yl]-1H-1,2,3-triazol-4-yl)-methoxylup-20(29)-en-3,28-diol; 30-(1-[galactos-1-yl]-1H-1,2,3-triazol-4-yl)-methoxylup-20(29)-en-3,28-diol; 30-(1-[mannos-1-yl]-1H-1,2,3-triazol-4-yl)-methoxylup- 20(29)-en-3,28-diol; 30-(1-[rhamnos-1-yl]-1H-1,2,3-triazol-4-yl)-methoxylup-20(29)-en-3,28-diol.

Preferred compounds of the invention are the following compounds, wherein X=$CH_2NH$; $R^1$=$C(O)CH_3$, $R^2$=$CH_2OC(O)CH_3$ Especially advantageous compounds are compounds selected from group: 30-1H-1,2,3-triazol-4-yl-methylaminolup-20(29)-en-3,28-diol diacetate; 30-(1-methyl-1H-1,2,3-triazol-4-yl)-methylaminolup-diacetate; 30-(1-ethyl-1H-1,2,3-triazol-4-yl)-methylaminolup-20(29)-en-3,28-diol diacetate; 30-(1-propyl-1H-1,2,3-triazol-4-yl)-methylaminolup-20(29)-en-3,28-diol diacetate; 30-(1-furyl-1H-1,2,3-triazol-4-yl)-methylaminolup-20(29)-en-3,28-diol diacetate; 30-(1-imidazolyl-1H-1,2,3-triazol-4-yl)-methylaminolup-20(29)-en-3,28-diol diacetate; 30-(1-phenyl-1H-1,2,3-triazol-4-yl)-methylaminolup-20(29)-en-3,28-diol diacetate; 30-(1-thiophenyl-1H-1,2,3-triazol-4-yl)-methylaminolup-20(29)-en-3,28-diol diacetate; 30-(1-[pyridin-2-yl]-1H-1,2,3-triazol-4-yl)-methylaminolup-20(29)-en-3,28-diol diacetate; 30-(1-[pyridin-3-yl]-1H-1,2,3-triazol-4-yl)-methylaminolup-20(29)-en-3,28-diol diacetate; 30-(1-[pyridin-4-yl]-1H-1,2,3-triazol-4-yl)-methylaminolup-20(29)-en-3,28-diol diacetate; 3041-[peracetyl glucos-1-yl]-1H-1,2,3-triazol-4-yl)-methylaminolup-20(29)-en-3,28-diol diacetate; 30-(1-[peracetyl galactos-1-yl]-1H-1,2,3-triazol-4-yl)-methylaminolup-20(29)-en-3,28-diol diacetate; 30-(1-[peracetyl mannos-1-yl]-1H-1,2,3-triazol-4-yl)-methylaminolup-20(29)-en-3,28-diol diacetate; 30-(1-[peracetyl rhamnos-1-yl]-1H-1,2,3-triazol-4-yl)-methylaminolup-20(29)-en-3,28-diol diacetate; 30-(1-[glucos-1-yl]-1H-1,2,3-triazol-4-yl)-methylaminolup-20(29)-en-3,28-diol diacetate; 30-(1-[galactos-1-yl]-1H-1,2,3-triazol-4-yl)-methylaminolup-20(29)-en-3,28-diol diacetate; 30-(1-[mannos-1-yl]-1H-1,2,3-triazol-4-yl)-methylaminolup-20(29)-en-3,28-diol diacetate; 30-(1-[rhamnos-1-yl]-1H-1,2,3-triazol-4-yl)-methylaminolup-20(29)-en-3,28-diol diacetate.

Preferred compounds of the invention are the following compounds, wherein X=$CH_2NH$; $R^1$=H, $R^2$=$CH_2OH$ Especially advantageous compounds are compounds selected from group: 30-1H-1,2,3-triazol-4-yl-methylaminolup-20(29)-en-3,28-diol; 30-(1-methyl-1H-1,2,3-triazol-4-yl)-methylaminolup-20(29)-en-3,28-diol; 30-(1-ethyl-1H-1,2,3-triazol-4-yl)-methylaminolup-20(29)-en-3,28-diol; 30-(1-propyl-1H-1,2,3-triazol-4-yl)-methylaminolup-20(29)-en-3,28-diol; 30-(1-furyl-1H-1,2,3-triazol-4-yl)-methylaminolup-20(29)-en-3,28-diol; 30-(1-imidazolyl-1H-1,2,3-triazol-4-yl)-methylaminolup-20(29)-en-3,28-diol; 30-(1-phenyl-1H-1,2,3-triazol-4-yl)-methylaminolup-20(29)-en-3,28-diol; 30-(1-thiophenyl-1H-1,2,3-triazol-4-yl)-methylaminolup-20(29)-en-3,28-diol; 30-(1-[pyridin-2-yl]-1H-1,2,3-triazol-4-yl)-methylaminolup-20(29)-en-3,28-diol; 30-(1-[pyridin-3-yl]-1H-1,2,3-triazol-4-yl)-methylaminolup-20(29)-en-3,28-diol; 30-(1-[pyridin-4-yl]-1H-1,2,3-triazol-4-yl)-methylaminolup-20(29)-en-3,28-diol; 30-(1-[peracetyl glucos-1-yl]-1H-1,2,3-triazol-4-yl)-methylaminolup-20(29)-en-3,28-diol; 30-(1-[peracetyl galactos-1-yl]-1H-1,2,3-triazol-4-yl)-methylaminolup-20(29)-en-3,28-diol; 30-(1-[peracetyl mannos-1-yl]-1H-1,2,3-triazol-4-yl)-methylaminolup-20(29)-en-3,28-diol; 30-(1-[peracetyl rhamnos-1-yl]-1H-1,2,3-triazol-4-yl)-methylaminolup-20(29)-en-3,28-diol; 30-(1-[glucos-1-yl]-1H-1,2,3-triazol-4-yl)-methylaminolup-20(29)-en-3,28-diol; 30-(1-[galactos-1-yl]-1H-1,2,3-triazol-4-yl)-methylaminolup-20(29)-en-3,28-diol; 30-(1-[mannos-1-yl]-1H-1,2,3-triazol-4-yl)-methylaminolup-20(29)-en-3,28-diol; 30-(1-[rhamnos-1-yl]-1H-1,2,3-triazol-4-yl)-methylaminolup-20(29)-en-3,28-diol.

Preferred compounds of the invention are the following compounds, wherein X=$CH_2NH$; $R^1$=H, $R^2$=COOH Especially advantageous compounds are compounds selected from group: 30-(1H-1,2,3-Triazol-4-yl-methylamino)-3β-hydroxylup-20(29)-en-28-oic acid; 30-[(1-methyl-1H-1,2,3-triazol-4-yl)-methylamino]-3β-hydroxylup-20(29)-en-28-oic acid; 30-[(1-ethyl-1H-1,2,3-triazol-4-yl)-methylamino]-3β-hydroxylup-20(29)-en-28-oic acid; 30-[(1-propyl-1H-1,2,3-triazol-4-yl)-methylamino]-3β-hydroxylup-20(29)-en-28-oic acid; 30-[(1-furyl-1H-1,2,3-triazol-4-yl)-methylamino]-3β-hydroxylup-20(29)-en-28-oic acid; 30-[(1-imidazolyl-1H-1,2,3-triazol-4-yl)-methylamino]-3β-hydroxylup-20(29)-en-28-oic acid; 30-[(1-phenyl-1H-1,2,3-triazol-4-yl)-methylamino]-3β-hydroxylup-20(29)-en-28-oic acid; 30-[(1-thiophenyl-1H-1,2,3-triazol-4-yl)-methylamino]-3β-hydroxylup-20(29)-en-28-oic acid; 30-[(1-[pyridin-2-yl]-1H-1,2,3-triazol-4-yl)-methylamino]-3β-hydroxylup-20(29)-en-28-oic acid; 30-{(1-[pyridin-3-yl]-1H-1,2,3-triazol-4-yl)-methylamino}-3β-hydroxylup-20(29)-en-28-oic acid; 30-{(1-[pyridin-4-yl]-1H-1,2,3-triazol-4-yl)-methylamino}-3β-hydroxylup-20(29)-en-28-oic acid; 30-{(1-[peracetyl glucos-1-yl]-1H-1,2,3-triazol-4-yl)-methylamino}-3β-hydroxylup-20(29)-en-28-oic acid; 30-{(1-[peracetyl galactos-1-yl]-1H-1,2,3-triazol-4-yl)-methylamino}-3β-hydroxylup-20(29)-en-28-oic acid; 30-{(1-[peracetyl mannos-1-yl]-1H-1,2,3-triazol-4-yl)-methylamino}-3β-hydroxylup-20(29)-en-28-oic acid; 30-{(1-[peracetyl rhamnos-1-yl]-1H-1,2,3-triazol-4-yl)-methylamino}-3β-hydroxylup-20(29)-en-28-oic acid; 30-{

(1-[glucos-1-yl]-1H-1,2,3-triazol-4-yl)-methylamino}-3β-hydroxylup-20(29)-en-28-oic acid; 30-{(1-[galactos-1-yl]-1H-1,2,3-triazol-4-yl)-methylamino}-3β-hydroxylup-20(29)-en-28-oic acid; 30-{(1-[mannos-1-yl]-1H-1,2,3-triazol-4-yl)-methylamino}-3β-hydroxylup-20(29)-en-28-oic acid; 30-{(1-[rhamnos-1-yl]-1H-1,2,3-triazol-4-yl)-methylamino}-3β-hydroxylup-20(29)-en-28-oic acid.

Preferred compounds of the invention are the following compounds, wherein X=$CH_2NH$; $R^1$=H, $R^2$=$COOCH_3$ Especially advantageous compounds are compounds selected from group: 30-(1H-1,2,3-triazol-4-yl-methylamino)-3β-hydroxylup-20(29)-en-28-oic acid methyl ester; 30-[(1-methyl-1H-1,2,3-triazol-4-yl)-methylamino]-3β-hydroxylup-20(29)-en-28-oic acid methyl ester; 30-[(1-ethyl-1H-1,2,3-triazol-4-yl)-methylamino]-3β-hydroxylup-20(29)-en-28-oic acid methyl ester; 30-[(1-propyl- 1H-1,2,3-triazol-4-yl)-methylamino]-3β-hydroxylup-20(29)-en-28-oic acid methyl ester; 30-[(1-furyl-1H-1,2,3-triazol-4-yl)-methylamino]-3β-hydroxylup-20(29)-en-28-oic acid methyl ester; 30-[(1-imidazolyl-1H-1,2,3-triazol-4-yl)-methylamino]-3β-hydroxylup-20(29)-en-28-oic acid methyl ester; 30-[(1-phenyl-1H-1,2,3-triazol-4-yl)-methylamino]-3β-hydroxylup-20(29)-en-28-oic acid methyl ester; 30-[(1-thiophenyl-1H-1,2,3-triazol-4-yl)-methylamino]-3β-hydroxylup-20(29)-en-28-oic acid methyl ester; 30-[(1-[pyridin-2-yl]-1H-1,2,3-triazol-4-yl)-methylamino]-3β-hydroxylup-20(29)-en-28-oic acid methyl ester; 30-{(1-[pyridin-3-yl]-1H-1,2,3-triazol-4-yl)-methylamino}-3β-hydroxylup-20(29)-en-28-oic acid methyl ester; 30-{(1-[pyridin-4-yl]-1H-1,2,3-triazol-4-yl)-methylamino}-3β-hydroxylup-20(29)-en-28-oic acid methyl ester; 30-{(1-[peracetyl glucos-1-yl]-1H-1,2,3-triazol-4-yl)-methylamino}-3β-hydroxylup-20(29)-en-28-oic acid methyl ester; 30-{(1-[peracetyl galactos-1-yl]-1H-1,2,3-triazol-4-yl)-methylamino}-3β-hydroxylup-20(29)-en-28-oic acid methyl ester; 30-{(1-[peracetyl mannos-1-yl]-1H-1,2,3-triazol-4-yl)-methylamino}-3β-hydroxylup-20(29)-en-28-oic acid methyl ester; 30-{(1-[peracetyl rhamnos-1-yl]-1H-1,2,3-triazol-4-yl)-methylamino}-3β-hydroxylup-20(29)-en-28-oic acid methyl ester; 30-{(1-[glucos-1-yl]-1H-1,2,3-triazol-4-yl)-methylamino}-3β-hydroxylup-20(29)-en-28-oic acid methyl ester; 30-{(1-[galactos-1-yl]-1H-1,2,3-triazol-4-yl)-methylamino}-3β-hydroxylup-20(29)-en-8-oic acid methyl ester; 30-{(1-[mannos-1-yl]-1H-1,2,3-triazol-4-yl)-methylamino}-3β-hydroxylup-20(29)-en-28-oic acid methyl ester; 30-{(1-[rhamnos-1-yl]-1H-1,2,3-triazol-4-yl)-methylamino}-3β-hydroxylup-20(29)-en-28-oic acid methyl ester.

Preferred compounds of the invention are the following compounds, wherein X=$CH_2O$; $R^1$=H, $R^2$=COOH Especially advantageous compounds are compounds selected from group: 30-(1H-1,2,3-triazol-4-yl-methoxy)-3β-hydroxylup-20(29)-en-28-oic acid; 30-[(1-methyl-1H-1,2,3-triazol-4-yl)-methoxyl-3β-hydroxylup-20(29)-en-28-oic acid; 30-[(1-ethyl-1H-1,2,3-triazol-4-yl)-methoxy]-3β-hydroxylup-20(29)-en-28-oic acid; 30-[(1-propyl-1H-1,2,3-triazol-4-yl)-methoxy]-3β-hydroxylup-20(29)-en-28-oic acid; 30-[(1-furyl-1H-1,2,3-triazol-4-yl)-methoxy]-3β-hydroxylup-20(29)-en-28-oic acid; 30-[(1-imidazolyl-1H-1,2,3-triazol-4-yl)-methoxy]-3β-hydroxylup-20(29)-en-28-oic acid; 304(1-phenyl-1H-1,2,3-triazol-4-yl)-methoxyl-3β-hydroxylup-20(29)-en-28-oic acid; 30-[(1-thiophenyl-1H-1,2,3-triazol-4-yl)-methoxy]-3β-hydroxylup-20(29)-en-28-oic acid; 304(1-[pyridin-2-yl]-1H-1,2,3-triazol-4-yl)-methoxy]-3β-hydroxylup-20(29)-en-28-oic acid; 30-{(1-[pyridin-3-yl]-1H-1,2,3-triazol-4-yl)-methoxy}-3β-hydroxylup-20(29)-en-28-oic acid; 30-{(1-[pyridin-4-yl]-1H-1,2,3-triazol-4-yl)-methoxy}-3β-hydroxylup-20(29)-en-28-oic acid; 30-{(1-[peracetyl glucos-1-yl]-1H-1,2,3-triazol-4-yl)-methoxy}-3β-hydroxylup-20(29)-en-28-oic acid; 30-{(1-[peracetyl galactos-1-yl]-1H-1,2,3-triazol-4-yl)-methoxy}-3β-hydroxylup-20(29)-en-28-oic acid; 30-{(1-[peracetyl mannos-1-yl]-1H-1,2,3-triazol-4-yl)-methoxy}-3β-hydroxylup-20(29)-en-28-oic acid; 30-{(1-[peracetyl rhamnos-1-yl]-1H-1,2,3-triazol-4-yl)-methoxy}-3β-hydroxylup-20(29)-en-28-oic acid; 30-{(1-[glucos-1-yl]-1H-1,2,3-triazol-4-yl)-methoxy}-3β-hydroxylup-20(29)-en-28-oic acid; 30-{(1-[galactos-1-yl]-1H-1,2,3-triazol-4-yl)-methoxy}-3β-hydroxylup-20(29)-en-28-oic acid; 30-{(1-[mannos-1-yl]-1H-1,2,3-triazol-4-yl)-methoxy}-3β-hydroxylup-20(29)-en-28-oic acid; 30-{(1-[rhamnos-1-yl]-1H-1,2,3-triazol-4-yl)-methoxy}-3β-hydroxylup-20(29)-en-28-oic acid.

Preferred compounds of the invention are the following compounds, wherein X=$CH_2O$; $R^1$=H, $R^2$=$COOCH_3$ Especially advantageous compounds are compounds selected from group: 30-(1H-1,2,3-triazol-4-yl-methoxy)-3β-hydroxylup-20(29)-en-28-oic acid methyl ester; 30-[(1-methyl-1H-1,2,3-triazol-4-yl)-methoxy]-3β-hydroxylup-20(29)-en-28-oic acid methyl ester; 30-[(1-ethyl-1H-1,2,3-triazol-4-yl)-methoxy]-3β-hydroxylup-20(29)-en-28-oic acid methyl ester; 30-[(1-propyl-1H-1,2,3-triazol-4-yl)-methoxy]-3β-hydroxylup-20(29)-en-28-oic acid methyl ester; 30-[(1-furyl-1H-1,2,3-triazol-4-yl)-methoxy]-3β-hydroxylup-20(29)-en-28-oic acid methyl ester; 30-[(1-imidazolyl-1H-1,2,3-triazol-4-yl)-methoxy]-3β-hydroxylup-20(29)-en-28-oic acid methyl ester; 30-[(1-phenyl-1H-1,2,3-triazol-4-yl)-methoxy]-3β-hydroxylup-20(29)-en-28-oic acid methyl ester; 30-[(1-thiophenyl-1H-1,2,3-triazol-4-yl)-methoxy]-3β-hydroxylup-20(29)-en-28-oic acid methyl ester; 30-[(1-[pyridin-2-yl]-1H-1,2,3-triazol-4-yl)-methoxy]-3β-hydroxylup-20(29)-en-28-oic acid methyl ester; 30-[(1-[pyridin-3-yl]-1H-1,2,3-triazol-4-yl)-methoxyl]-3β-hydroxylup-20(29)-en-28-oic acid methyl ester; 30-{(1-[pyridin-4-yl]-1H-1,2,3-triazol-4-yl)-methoxy}-3β-hydroxylup-20(29)-en-28-oic acid methyl ester; 30-{(1-[peracetyl glucos-1-yl]-1H-1,2,3-triazol-4-yl)-methoxy}-3β-hydroxylup-20(29)-en-28-oic acid methyl ester; 30-{(1-[peracetyl galactos-1-yl]-1H-1,2,3-triazol-4-yl)-methoxy}-3β-hydroxylup-20(29)-en-28-oic acid methyl ester; 30-{(1-[peracetyl mannos-1-yl]-1H-1,2,3-triazol-4-yl)-methoxy}-3β-hydroxylup-20(29)-en-28-oic acid methyl ester; 30-{(1-[peracetyl rhamnos-1-yl]-1H-1,2,3-triazol-4-yl)-methoxy}-3β-hydroxylup-20(29)-en-28-oic acid methyl ester; 30-{(1-[glucos-1-yl]-1H-1,2,3-triazol-4-yl)-methoxy}-3β-hydroxylup-20(29)-en-28-oic acid methyl ester; 30-{(1-[galactos-1-yl]-1H-1,2,3-triazol-4-yl)-methoxy}-3β-hydroxylup-20(29)-en-28-oic acid methyl ester; 30-{(1-[mannos-1-yl]-1H-1,2,3-triazol-4-yl)-methoxy}-3β-hydroxylup-20(29)-en-28-oic acid methyl ester; 30-{(1-[rhamnos-1-yl]-1H-1,2,3-triazol-4-yl)-methoxy}-3β-hydroxylup-20(29)-en-28-oic acid methyl ester.

Preferred compounds of the invention are the following compounds, wherein X=CONH; $R^1$=$C(O)CH_3$, $R^2$=$CH_2O$ $C(O)CH_3$ Especially advantageous compounds are compounds selected from group: 30-1H-1,2,3-triazol-4-yl-methylamino, 30-oxolup-20(29)-en-3,28-diol diacetate; 30-(1-methyl-1H-1,2,3-triazol-4-yl)-methylamino,30-oxolup-20(29)-en-3,28-diol diacetate; 30-(1-ethyl-1H-1,2,3-triazol-4-yl)-methylamino,30-oxolup-20(29)-en-3,28-diol diacetate; 30-(1-propyl-1H-1,2,3-triazol-4-yl)-methylamino,30-oxolup-20(29)-en-3,28-diol diacetate; 30-(1-furyl-1H-1,2,3-triazol-4-yl)-methylamino,30-oxolup-20(29)-en-3,28-diol diacetate; 30-(1-imidazolyl-1H-1,2,3-triazol-4-yl)-methylamino,30-oxolup-20(29)-en-3,28-diol diacetate; 30-(1-phenyl-1H-1,2,3-triazol-4-yl)-methylamino,30-oxolup-20(29)-en-3,28-diol diacetate; 30-(1-thiophenyl-1H-1,2,3-triazol-4-yl)-methylamino,30-oxolup-20(29)-en-3,28-diol diacetate; 30-(1-[pyridin-2-yl]-1H-1,2,3-triazol-4-yl)-methylamino, 30-oxolup-20(29)-en-3,28-diol diacetate; 30-(1-[pyridin-3-yl]-1H-1,2,3-triazol-4-yl)-methylamin,30-oxoolup-20(29)-en-3,28-diol diacetate; 30-(1-[pyridin-4-yl]-1H-1,2,3-triazol-4-yl)-methylamino,30-oxolup-20(29)-en-3,28-diol diacetate; 30-(1-[peracetyl glucos-1-yl]-1H-1,2,3-triazol-4-yl)-methylamino,30-oxolup-20(29)-en-3,28-diol diacetate; 30-(1-[peracetyl galactos-1-yl]-1H-1,2,3-triazol-4-yl)-methylamino,30-oxolup-20(29)-en-3,28-diol diacetate; 30-(1-[peracetyl mannos-1-yl]-1H-1,2,3-triazol-4-yl)-methylamino,30-oxolup-20(29)-en-3,28-diol diacetate; 30-(1-[peracetyl rhamnos-1-yl]-1H-1,2,3-triazol-4-yl)-methylamino,30-oxolup-20(29)-en-3,28-diol diacetate; 30-(1-[glucos-1-yl]-1H-1,2,3-triazol-4-yl)-methylamino,30-oxolup-20(29)-en-3,28-diol diacetate; 30-(1-[galactos-1-yl]-1H-1,2,3-triazol-4-yl)-methylamino,30-oxolup-20(29)-en-3,28-diol diacetate; 30-(1-[mannos-1-yl]-1H-1,2,3-triazol-4-yl)-methylamino,30-oxolup-20(29)-en-3,28-diol diacetate; 30-(1-[rhamnos-1-yl]-1H-1,2,3-triazol-4-yl)-methylamino,30-oxolup-20(29)-en-3,28-diol diacetate.

Preferred compounds of the invention are the following compounds, wherein X=CONH; $R^1$=H, $R^2$=$CH_2OH$ Especially advantageous compounds are compounds selected from group: 30-1H-1,2,3-triazol-4-yl-methylamino, 30-oxolup-20(29)-en-3,28-diol; 30-(1-methyl-1H-1,2,3-triazol-4-yl)-methylamino,30-oxolup-20(29)-en-3,28-diol; 30-(1-ethyl-1H-1,2,3-triazol-4-yl)-methylamino,30-oxolup-20(29)-en-3,28-diol; 30-(1-propyl-1H-1,2,3-triazol-4-yl)-methylamino,30-oxolup-20(29)-en-3,28-diol; 30-(1-furyl-1H-1,2,3-triazol-4-yl)-methylamino,30-oxolup-20(29)-en-3,28-diol; 30-(1-imidazolyl-1H-1,2,3-triazol-4-yl)-methylamino,30-oxolup-20(29)-en-3,28-diol; 30-(1-phenyl-1H-1,2,3-triazol-4-yl)-methylamino,30-oxolup-20(29)-en-3,28-diol; 30-(1-thiophenyl-1H-1,2,3-triazol-4-yl)-methylamino,30-oxolup-20(29)-en-3,28-diol; 30-(1-[pyridin-2-yl]-1H-1,2,3-triazol-4-yl)-methylamino,30-oxolup-20(29)-en-3,28-diol; 30-(1-[pyridin-3-yl]-1H-1,2,3-triazol-4-yl)-methylamino,30-oxolup-20(29)-en-3,28-diol; 30-(1-[pyridin-4-yl]-1H-1,2,3-triazol-4-yl)-methylamino, 30-oxolup-20(29)-en-3,28-diol; 30-(1-[peracetyl glucos-1-yl]-1H-1,2,3-triazol-4-yl)-methylamino,30-oxolup-20(29)-en-3,28-diol; 30-(1-[peracetyl galactos-1-yl]-1H-1,2,3-triazol-4-yl)-methylamino,30-oxolup-20(29)-en-3,28-diol; 30-(1-[peracetyl mannos-1-yl]-1H-1,2,3-triazol-4-yl)-methylamino,30-oxolup-20(29)-en-3,28-diol; 30-(1-[peracetyl rhamnos-1-yl]-1H-1,2,3-triazol-4-yl)-methylamino,30-oxolup-20(29)-en-3,28-diol; 30-(1-[glucos-1-yl]-1H-1,2,3-triazol-4-yl)-methylamino,30-oxolup-20(29)-en-3,28-diol; 30-(1-[galactos-1-yl]-1H-1,2,3-triazol-4-yl)-methylamino,30-oxolup-20(29)-en-3,28-diol; 30-(1-[mannos-1-yl]-1H-1,2,3-triazol-4-yl)-methylamino,30-oxolup-20(29)-en-3,28-diol; 30-(1-[rhamnos-1-yl]-1H-1,2,3-triazol-4-yl)-methylamino, 30-oxolup-20(29)-en-3,28-diol.

Preferred compounds of the invention are the following compounds, wherein X=CONH; $R^1$=H, $R^2$=COOH Especially advantageous compounds are compounds selected from group: 30-(1H-1,2,3-triazol-4-yl-methylamino)-3β-hydroxy,30-oxolup-20(29)-en-28-oic acid; 30-[(1-methyl-1H-1,2,3-triazol-4-yl)-methylamino]-3β-hydroxy,30-oxolup-20(29)-en-28-oic acid; 30-[(1-ethyl-1H-1,2,3-triazol-4-yl)-methylamino]-3β-hydroxy,30-oxolup-20(29)-en-28-oic acid; 30-[(1-propyl-1H-1,2,3-triazol-4-yl)-methylamino]-3β-hydroxy,30-oxolup-20(29)-en-28-oic acid; 30-[(1-furyl-1H-1,2,3-triazol-4-yl)-methylamino]-3β-hydroxy,30-oxolup-20(29)-en-28-oic acid; 30-[(1-imidazolyl-1H-1,2,3-triazol-4-yl)-methylamino]-3β-hydroxy,30-oxolup-20(29)-en-28-oic acid; 30-[(1-phenyl-1H-1,2,3-triazol-4-yl)-methylamino]-3β-hydroxy,30-oxolup-20(29)-en-28-oic acid; 30-[(1-thiophenyl-1H-1,2,3-triazol-4-yl)-methylamino]-3β-hydroxy,30-oxolup-20(29)-en-28-oic acid; 30-[(1-[pyridin-2-yl]-1H-1,2,3-triazol-4-yl)-methylamino]-3β-hydroxy,30-oxolup-20(29)-en-28-oic acid; 30-{(1-[pyridin-3-yl]-1H-1,2,3-triazol-4-yl)-methylamino}-3β-hydroxy,30-oxolup-20(29)-en-28-oic acid; 30-{(1-[pyridin-4-yl]-1H-1,2,3-triazol-4-yl)-methylamino}-3β-hydroxy,30-oxolup-20(29)-en-28-oic acid; 30-{(1-[peracetyl glucos-1-yl]-1H-1,2,3-triazol-4-yl)-methylamino}-3β-hydroxy,30-oxolup-20(29)-en-28-oic acid; 30-{(1-[peracetyl galactos-1-yl]-1H-1,2,3-triazol-4-yl)-methylamino}-3β-hydroxy,30-oxolup-20(29)-en-28-oic acid; 30-{(1-[peracetyl mannos-1-yl]-1H-1,2,3-triazol-4-yl)-methylamino}-3β-hydroxy,30-oxolup-20(29)-en-28-oic acid; 30-{(1-[peracetyl rhamnos-1-yl]-1H-1,2,3-triazol-4-yl)-methylamino}-3β-hydroxy,30-oxolup-20(29)-en-28-oic acid; 30-{(1-[glucos-1-yl]-1H-1,2,3-triazol-4-yl)-methylamino}-3β-hydroxy,30-oxolup-20(29)-en-28-oic acid; 30-{(1-[galactos-1-yl]-1H-1,2,3-triazol-4-yl)-methylamino}-3β-hydroxy,30-oxolup-20(29)-en-28-oic acid; 30-{(1-[mannos-1-yl]-1H-1,2,3-triazol-4-yl)-methylamino}-3β-hydroxy,30-oxolup-20(29)-en-28-oic acid; 30-{(1-[rhamnos-1-yl]-1H-1,2,3-triazol-4-yl)-methylamino}-3β-hydroxy,30-oxolup-20(29)-en-28-oic acid.

Preferred compounds of the invention are the following compounds, wherein X=CONH; $R^1$=OH, $R^2$=$COOCH_3$ Especially advantageous compounds are compounds selected from group: 30-(1H-1,2,3-triazol-4-yl-methylamino)-3β-hydroxy,30-oxolup-20(29)-en-28-oic acid methyl ester; 30-[(1-methyl-1H-1,2,3-triazol-4-yl)-methylamino]-3β-hydroxy,30-oxolup-20(29)-en-28-oic acid methyl ester; 30-[(1-ethyl-1H-1,2,3-triazol-4-yl)-methylamino]-3β-hydroxy,30-oxolup-20(29)-en-28-oic acid methyl ester; 30-[(1-propyl-1H-1,2,3-triazol-4-yl)-methylamino]-3β-hydroxy,30-oxolup-20(29)-en-28-oic acid methyl ester; 30-[(1-furyl-1H-1,2,3-triazol-4-yl)-methylamino]-3β-hydroxy,30-oxolup-20(29)-en-28-oic acid methyl ester; 30-[(1-imidazolyl-1H-1,2,3-triazol-4-yl)-methylamino]-3β-hydroxy,30-oxolup-20(29)-en-28-oic acid methyl ester; 30-[(1-phenyl-1H-1,2,3-triazol-4-yl)-methylamino]-3β-hydroxy,30-oxolup-20(29)-en-28-oic acid methyl ester; 30-[(1-thiophenyl-1H-1,2,3-triazol-4-yl)-methylamino]-30-hydroxy,30-oxolup-20(29)-en-28-oic acid methyl ester; 30-[(1-[pyridin-2-yl]-1H-1,2,3-triazol-4-yl)-methylamino]-3β-hydroxy,30-oxolup-20(29)-en-28-oic acid methyl ester; 30-{(1-[pyridin-3-yl]-1H-1,2,3-triazol-4-yl)-methylamino}-3β-hydroxy,30-oxolup-20(29)-en-28-oic acid methyl ester; 30-{(1-[pyridin-4-yl]-1H-1,2,3-triazol-4-yl)-methylamino}-3β-hydroxy,30-oxolup-20(29)-en-28-oic acid methyl ester; 30-{(1-[peracetyl glucos-1-yl]-1H-1,2,3-triazol-4-yl)-methylamino}-3β-hydroxy,30-oxolup-20(29)-en-28-oic acid methyl ester; 30-{(1-[peracetyl galactos-1-yl]-1H-1,2,3-triazol-4-yl)-methylamino}-3β-hydroxy,30-oxolup-20(29)-en-28-oic acid methyl ester; 30-{(1-[peracetyl mannos-1-yl]-1H-1,2,3-triazol-4-yl)-methylamino}-3β-hydroxy,30-oxolup-20(29)-en-28-oic acid methyl ester; 30-{(1-[peracetyl rhamnos-1-yl]-1H-1,2,3-triazol-4-yl)-methylamino}-3β-hydroxy,30-oxolup-20(29)-en-28-oic acid methyl ester; 30-{(1-[glucos-1-yl]-1H-1,2,3-triazol-4-yl)-methylamino}-3β-hydroxy,30-oxolup-20(29)-en-28-oic acid methyl ester; 30-{(1-[galactos-1-yl]-1H-1,2,3-triazol-4-yl)-methylamino}-3β-hydroxy,30-oxolup-20(29)-en-28-oic acid methyl ester; 30-{(1-[mannos-1-yl]-1H-

1,2,3-triazol-4-yl)-methylamino}-3β-hydroxy,30-oxolup-20(29)-en-28-oic acid methyl ester; 30-{(1-[rhamnos-1-yl]-1H-1,2,3-triazol-4-yl)-methylamino}-3β-hydroxy,30-oxolup-20(29)-en-28-oic acid methyl ester.

Preferred compounds of the invention are the following compounds, wherein X=C(O)O; $R^1$=C(O)$CH_3$, $R^2$=$CH_2$OC(O)$CH_3$ Especially advantageous compounds are compounds selected from group: pyridin-2-yl-methyl 3β,28-diacetoxylup-20(29)-en-30-oate; pyridin-3-yl-methyl 3β,28-diacetoxylup-20(29)-en-30-oate; pyridin-4-yl-methyl 3β,28-diacetoxylup-20(29)-en-30-oate; furan-2-yl-methyl 3β,28-diacetoxylup-20(29)-en-furan-3-yl-methyl 3β,28-diacetoxylup-20(29)-en-30-oate; thiophen-2-yl-methyl 3β,28-diacetoxylup-20(29)-en-30-oate; thiophen-3-yl-methyl 3β,28-diacetoxylup-20(29)-en-30-oate; pyrrol-2-yl-methyl 3β,28-diacetoxylup-20(29)-en-30-oate; pyrrol-3-yl-methyl 3β,28-diacetoxylup-20(29)-en-pyrrazol-3-yl-methyl 3β,28-diacetoxylup-20(29)-en-30-oate; pyrrazol-4-yl-methyl 3β,28-diacetoxylup-20(29)-en-30-oate; oxazol-3-yl-methyl 3β,28-diacetoxylup-20(29)-en-30-oate; oxazol-4-yl-methyl 3β,28-diacetoxylup-20(29)-en-30-oate; isoxazol-4-yl-methyl 3β,28-diacetoxylup-20(29)-en-30-oate; imidazole-3-yl-methyl 3β,28-diacetoxylup-20(29)-en-30-oate; imidazole-4-yl-methyl 3β,28-diacetoxylup-20(29)-en-30-oate; thiazol-4-yl-methyl 3β,28-diacetoxylup-20(29)-en-30-oate; isothiazol-3-yl-methyl 3β,28-diacetoxylup-20(29)-en-30-oate; isothiazol-4-yl-methyl 3β,28-diacetoxylup-20(29)-en-30-oate; 1H-1,2,3-triazol-4-yl-methyl 3β,28-diacetoxylup-20(29)-en-30-oate.

and the pharmaceutically acceptable salts thereof, in particular salts with alkali metals, ammonium or amines, or addition salts with acids.

In case there is an enantiomeric carbon in the molecule, this invention includes also racemates as well as optically active isomers and their mixtures.

Generally, the most preferred compounds of the general formula I are: 30-1H-1,2,3-triazol-4-yl-methoxylup-20(29)-en-3,28-diol diacetate, 30-(1-methyl1H-1,2,3-triazol-4-yl)-methoxylup-20(29)-en-3,28-diol diacetate, 30-(1-phenyl1H-1,2,3-triazol-4-yl)-methoxylup-20(29)-en-3,28-diol diacetate, 30-(1-[pyridin-2-yl]-1H-1,2,3-triazol-4-yl)-methoxylup-20(29)-en-3,28-diol diacetate, 30-(1-[peracetyl glucos-1-yl]-1H-1,2,3-triazol-4-yl)-methoxylup-20(29)-en-3,28-diol diacetate, 30-(1-[peracetyl galactos-1-yl]-1H-1,2,3-triazol-4-yl)-methoxylup-20(29)-en-3,28-diol diacetate, 30-(1-[glucos-1-yl]-1H-1,2,3-triazol-4-yl)-methoxylup-20(29)-en-3,28-diol diacetate, 30-(1-[galactos-1-yl]-1H-1,2,3-triazol-4-yl)-methoxylup-20(29)-en-3,28-diol diacetate, 30-1H-1,2,3-triazol-4-yl-methoxylup-20(29)-en-3,28-diol, 30-(1-methyl1H-1,2,3-triazol-4-yl)-methoxylup-20(29)-en-3,28-diol, 30-(1-[peracetyl galactos-1-yl]-1H-1,2,3-triazol-4-yl)-methoxylup-20(29)-en-3,28-diol, 30-(1-[galactos-1-yl]-1H-1,2,3-triazol-4-yl)-methoxylup-20(29)-en-3,28-diol, 30-1H-1,2,3-triazol-4-yl-methylaminolup-20(29)-en-3,28-diol diacetate, 30-(1-methyl1H-1,2,3-triazol-4-yl)-methylaminolup-20(29)-en-3,28-diol diacetate, [peracetyl glucos-1-yl]-1H-1,2,3-triazol-4-yl)-methylaminolup-20(29)-en-3,28-diol diacetate, [peracetyl galactos-1-yl]-1H-1,2,3-triazol-4-yl)-methylaminolup-20(29)-en-3,28-diol diacetate, [glucos-1-yl]-1H-1,2,3-triazol-4-yl)-methylaminolup-20(29)-en-3,28-diol diacetate, 30-(1-[galactos-1-yl]-1H-1,2,3-triazol-4-yl)-methylaminolup-20(29)-en-3,28-diol diacetate, 30-1H-1,2,3-triazol-4-yl-methylaminolup-20(29)-en-3,28-diol, 30-(1-methyl1H-1,2,3-triazol-4-yl)-methylaminolup-20(29)-en-3,28-diol, 30-(1-[peracetyl glucos-1-yl]-1H-1,2,3-triazol-4-yl)-methylaminolup-20(29)-en-3,28-diol, 30-(1-[peracetyl galactos-1-yl]-1H-1,2,3-triazol-4-yl)-methylaminolup-20(29)-en-3,28-diol, 30-(1-[glucos-1-yl]-1H-1,2,3-triazol-4-yl)-methylaminolup-30-(1-[galactos-1-yl]-1H-1,2,3-triazol-4-yl)-methylaminolup-20(29)-en-3,28-diol, 30-(1H-1,2,3-triazol-4-yl-methylamino)-3β-hydroxylup-20(29)-en-28-oic acid, 30-[(1-methyl1H-1,2,3-triazol-4-yl)-methylamino]-3β-hydroxylup-20(29)-en-28-oic acid, 30-{(1-[peracetyl glucos-1-yl]-1H-1,2,3-triazol-4-yl)-methylamino}-3β-hydroxylup-20(29)-en-28-oic acid, 30-{(1-[peracetyl galactos-1-yl]-1H-1,2,3-triazol-4-yl)-methylamino}-3β-hydroxylup-20(29)-en-28-oic acid, 30-{(1-[glucos-1-yl]-1H-1,2,3-triazol-4-yl)-methylamino}-3β-hydroxylup-20(29)-en-28-oic acid, 30-{(1-[galactos-1-yl]-1H-1,2,3-triazol-4-yl)-methylamino}-3β-hydroxylup-20(29)-en-28-oic acid, 30-(1H-1,2,3-triazol-4-yl-methylamino)-3β-hydroxylup-20(29)-en-28-oic acid methyl ester, 30-(1H-1,2,3-triazol-4-yl-methoxy)-3β-hydroxylup-20(29)-en-28-oic acid, 30-{(1-[peracetyl galactos-1-yl]-1H-1,2,3-triazol-4-yl)-methoxy}-3β-hydroxylup-20(29)-en-28-oic acid, 30-{(1-[galactos-1-yl]-1H-1,2,3-triazol-4-yl)-methoxy}-3β-hydroxylup-20(29)-en-28-oic acid, 30-(1H-1,2,3-triazol-4-yl-methoxy)-3β-hydroxylup-20(29)-en-28-oic acid methyl ester, 30-{(1-[peracetyl glucos-1-yl]-1H-1,2,3-triazol-4-yl)-methoxy}-3β-hydroxylup-20(29)-en-28-oic acid methyl ester, 30-{(1-[galactos-1-yl]-1H-1,2,3-triazol-4-yl)-methoxy}-3β-hydroxylup-20(29)-en-28-oic acid methyl ester, 30-1H-1,2,3-triazol-4-yl-methylamino,30-oxolup-20(29)-en-3,28-diol diacetate, 30-(1-[peracetyl glucos-1-yl]-1H-1,2,3-triazol-4-yl)-methylamino,30-oxolup-20(29)-en-3,28-diol diacetate, 30-(1-[glucos-1-yl]-1H-1,2,3-triazol-4-yl)-methylamino,30-oxolup-20(29)-en-3,28-diol diacetate, 30-1H-1,2,3-triazol-4-yl-methylamino,30-oxolup-20(29)-en-3,28-diol, 30-(1-[peracetyl glucos-1-yl]-1H-1,2,3-triazol-4-yl)-methylamino,30-oxolup-20(29)-en-3,28-diol, 30-(1-[glucos-1-yl]-1H-1,2,3-triazol-4-yl)-methylamino,30-oxolup-20(29)-en-3,28-diol, 30-(1H-1,2,3-triazol-4-yl-methylamino)-3β-hydroxy,30-oxolup-20(29)-en-28-oic acid, 30-{(1-[peracetyl galactos-1-yl]-1H-1,2,3-triazol-4-yl)-methylamino}-3β-hydroxy,30-oxolup-20(29)-en-28-oic acid, 30-{(1-[galactos-1-yl]-1H-1,2,3-triazol-4-yl)-methylamino}-3β-hydroxy,30-oxolup-20(29)-en-28-oic acid, 30-(1H-1,2,3-triazol-4-yl-methylamino)-3β-hydroxy,30-oxolup-20(29)-en-28-oic acid methyl ester, 30-{(1-[peracetyl galactos-1-yl]-1H-1,2,3-triazol-4-yl)-methylamino}-3β-hydroxy,30-oxolup-20(29)-en-28-oic acid methyl ester, 30-{(1-[galactos-1-yl]-1H-1,2,3-triazol-4-yl)-methylamino}-3β-hydroxy,30-oxolup-20(29)-en-28-oic acid methyl ester, pyridin-2-yl-methyl 3β,28-diacetoxylup-20(29)-en-30-oate, pyridin-3-yl-methyl 3β,28-diacetoxylup-20(29)-en-30-oate, pyridin-4-yl-methyl 3β,28-diacetoxylup-20(29)-en-30-oate, furan-2-yl-methyl 3β,28-diacetoxylup-20(29)-en-30-oate, furan-3-yl-methyl 3β,28-diacetoxylup-20(29)-en-30-oate, thiophen-2-yl-methyl 3β,28-diacetoxylup-20(29)-en-30-oate, thiophen-2-yl-methyl 3β,28-diacetoxylup-20(29)-en-30-oate, and 1,2,3-1H-1,2,3-triazol-4-yl-methyl 3β,28-diacetoxylup-20(29)-en-30-oate.

The compounds of the present invention have a wide range of biological activities, including activities in increasing viability of neuronal cells, reducing oxidative stress, neuroprotectivity and antiapoptotic activation, which are especially useful in pharmaceutical applications to treat neurodegenerative diseases and correspond to the spectrum of effects required of the agents intended for such treatment.

The present invention also provides the compounds of the general formula I for use as medicaments.

The invention preferably relates to the compounds of the general formula I for use in the treatment or prophylaxis of neurodegenerative diseases, in particular selected from amyotrophic lateral sclerosis, Parkinson's disease, Alzheimer's disease, Huntington's disease, progressive supranuclear palsy, corticobasal degeneration, frontotemporal dementia, Lewy body dementia, multiple system atrophy, chronic traumatic encephalopathy, spinocerebellar ataxias.

In a preferred embodiment, the invention provides the compounds of the general formula I for use in the treatment and prophylaxis of Parkinson's disease.

The present invention further provides pharmaceutical compositions comprising one or more compounds of the general formula I together with at least one pharmaceutically acceptable carrier.

Pharmaceutical Compositions

Suitable routes for administration include oral, rectal, topical (including dermal, ocular, buccal and sublingual), vaginal and parenteral (including subcutaneous, intramuscular, intravitreous, intravenous, intradermal, intrathecal and epidural).

The therapeutic compositions generally comprise about 1% to about 95% of the active ingredient. Single-dose forms of administration preferably comprise about 20% to about 90% of the active ingredient and administration forms which are not single-dose preferably comprise about 5% to about 20% of the active ingredient. Unit dose forms are, for example, coated tablets, tablets, ampoules, vials, suppositories or capsules. Other forms of administration are, for example, ointments, creams, pastes, foams, tinctures, lipsticks, drops, sprays, dispersions and the like. Examples are capsules containing from about 0.05 g to about 1.0 g of the active ingredient.

The pharmaceutical and cosmetic compositions of the present invention are prepared in a manner known per se, for example by means of conventional mixing, granulating, coating, dissolving or lyophilizing processes.

Preferably, solutions of the active ingredient, and in addition also suspensions or dispersions, especially isotonic aqueous solutions, dispersions or suspensions, are used, it being possible for these to be prepared before use, for example in the case of lyophilized compositions which comprise the active substance by itself or together with a carrier, for example mannitol. The compositions can be sterilized and/or comprise excipients, for example preservatives, stabilizers, wetting agents and/or emulsifiers, solubilizing agents, salts for regulating the osmotic pressure and/or buffers, and they are prepared in a manner known per se, for example by means of conventional dissolving or lyophilizing processes. The solutions or suspensions mentioned can comprise viscosity-increasing substances, such as sodium carboxymethylcellulose, carboxymethylcellulose, dextran, polyvinylpyrrolidone or gelatin.

Suspensions in oil comprise, as the oily component, vegetable, synthetic or semi-synthetic oils customary for injection purposes. Oils which may be mentioned are, in particular, liquid fatty acid esters which contain, as the acid component, a long-chain fatty acid having 8-22, in particular 12-22, carbon atoms (e.g., lauric acid, tridecylic acid, myristic acid, pentadecylic acid, palmitic acid, margaric acid, stearic acid, acid, arachidonic acid, behenic acid, and the like) or corresponding unsaturated acids (e.g., oleic acid, elaidic acid, euric acid, brasidic acid or linoleic acid). Other additional ingredients known in the art can be included if desired (e.g., antioxidants such as vitamin E, β-carotene, or 3,5-di-tert-butyl-4-hydroxytoluene, and the like). The alcohol component of these fatty acid esters generally contains no more than about 6 carbon atoms and can be mono- or polyhydric. Mono-, di-, or trihydric alcohols such as methanol, ethanol, propanol, butanol, or pentanol, or isomers thereof, can be used; glycols and glycerols are generally preferred. Fatty acid esters can therefore include, for example, ethyl oleate, isopropyl myristate, isopropyl palmitate, "Labrafil M 2375" (polyoxyethylene glycerol trioleate from Gattefoseé, Paris), "Labrafil M 1944 CS" (unsaturated polyglycolated glycerides prepared by an alcoholysis of apricot kernel oil and made up of glycerides and polyethylene glycol esters; from Gattefoseé, Paris), "Labrasol" (saturated polyglycolated glycerides prepared by an alcoholysis of TCM and made up of glycerides and polyethylene glycol esters; from Gattefoseé, Paris), and/or "Miglyol 812" (triglyceride of saturated fatty acids of chain length C8 to C12 from Hüls AG, Germany), and in particular vegetable oils, such as cottonseed oil, almond oil, olive oil, castor oil, sesame oil, soybean oil and, in particular, groundnut oil as well as mixtures thereof.

The preparation of the compositions intended for human use should, of course, be carried out in the customary and approved manner under sterile conditions, and maintained under appropriate conditions up to and including the time of use.

For example, pharmaceutical compositions for oral use can be obtained by combining the active ingredient with one or more solid carriers, if appropriate granulating the resulting mixture, and, if desired, processing the mixture or granules to tablets or coated tablet cores, if appropriate by addition of additional excipients. Suitable carriers are, in particular, fillers, such as sugars, for example lactose, sucrose, mannitol or sorbitol, cellulose preparations and/or calcium phosphates, for example tricalcium diphosphate, or calcium hydrogen phosphate, and furthermore binders, such as starches, for example maize, wheat, rice or potato starch, methylcellulose, hydroxypropylmethylcellulose, sodium carboxymethylcellulose and/or polyvinylpyrrolidone, and/or, if desired, desintegrators, such as the above mentioned starches, and furthermore carboxymethyl-starch, cross-linked polyvinylpyrrolidone, alginic acid or a salt thereof, such as sodium alginate. Additional excipients are, in particular, flow regulators and lubricants, for example salicylic acid, talc, stearic acid or salts thereof, such as magnesium stearate or calcium stearate, and/or polyethylene glycol, or derivatives thereof.

Coated tablet cores can be provided with suitable coatings which, if appropriate, are resistant to gastric juice, the coatings used being, inter alia, concentrated sugar solutions, which, if appropriate, comprise gum arabic, talc, polyvinylpyrrolidone, polyethylene glycol and/or titanium dioxide, coating solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate. Dyes or pigments can be admixed to the tablets or coated tablet coatings, for example for identification or characterization of different doses of active ingredient.

Pharmaceutical compositions, which can be used orally, can also be in the form hard capsules of gelatine and soft, closed capsules of gelatine and a plasticizer, such as glycerol or sorbitol. The hard capsules can contain the active ingredient in the form of granules, mixed for example with fillers, such as maize starch, binders and/or lubricants, such as talc or magnesium stearate, and stabilizers if appropriate. In soft capsules, the active ingredient is preferably dissolved or suspended in suitable liquid excipients, such as greasy oils, paraffin oil or liquid polyethylene glycol's or fatty acid esters of ethylene glycol or propylene glycol, it being likewise possible to add stabilizers and detergents such as, for example, the polyethylene sorbitan fatty acid ester type.

Other oral forms of administration include, for example, syrups prepared in the customary manner, which comprise the active ingredient, for example, in suspended form and in a concentration of about 5% to 20%, preferably about 10% or in a similar concentration which results in a suitable individual dose, for example, when 5 or 10 mL are measured out. Other forms include pulverulent or liquid concentrates for preparing shakes, beverages, and the like. Such concentrates can also be packed in unit dose quantities.

Pharmaceutical compositions, which can be used rectally, are, for example, suppositories that comprise a combination of the active ingredient with a suppository base. Suitable suppository bases are, for example, naturally occurring or synthetic triglycerides, paraffin hydrocarbons, polyethylene glycols or higher alkanols.

Compositions which are suitable for parental administration are aqueous solutions of an active ingredient in water-soluble form, for example of water-soluble salt, or aqueous injection suspensions, which comprise viscosity-increasing substances, for example sodium carboxymethylcellulose, sorbitol and/or dextran, and if appropriate, stabilizers. The active ingredient can also be present here in the form of a lyophilizate, if appropriate together with excipients, and be dissolved before parenteral administration by addition of suitable solvents. Solutions such as are used, for example, for parental administration can also be used as infusion solutions. Preferred preservatives are, for example antioxidants, such as ascorbic acid, or microbicides, such as sorbic or benzoic acid.

Ointments are oil-in-water emulsions, which comprise not more than 70%, but preferably 20-50% of water or aqueous phase. The fatty phase consists, in particular, hydrocarbons, for example vaseline, paraffin oil or hard paraffin's, which preferably comprise suitable hydroxy compounds, such as fatty alcohol's or esters thereof, for example cetyl alcohol or wool wax alcohols, such as wool wax, to improve the water-binding capacity. Emulsifiers are corresponding lipophilic substances, such as sorbitan fatty acid esters (Spans), for example sorbitan oleate and/or sorbitan isostearate. Additives to the aqueous phase are, for example, humectants, such as polyalcohols, for example, glycerol, propylene glycol, sorbitol and/or polyethylene glycol, or preservatives and odoriferous substances.

Fatty ointments are anhydrous and comprise, as the base, in particular, hydrocarbons, for example paraffin, vaseline or paraffin oil, and furthermore naturally occurring or semi-synthetic fats, for example, hydrogenated coconut-fatty acid triglycerides, or, preferably, hydrogenated oils, for example hydrogenated groundnut or castor oil, and furthermore fatty acid partial esters of glycerol, for example glycerol mono- and/or distearate, and for example, the fatty alcohols. They also can contain emulsifiers and/or additives mentioned in connection with the ointments which increase uptake of water.

Creams are oil-in-water emulsions, which comprise more than 50% of water. Oily bases used are, in particular, fatty alcohols, for example, lauryl, cetyl or stearyl alcohols, fatty acids, for example palmitic or stearic acid, liquid to solid waxes, for example isopropyl myristate, wool wax or beeswax, and/or hydrocarbons, for example vaseline (petrolatum) or paraffin oil. Emulsifiers are surface-active substances with predominantly hydrophilic properties, such as corresponding non-ionic emulsifiers, for example fatty acid esters of polyalcohols or ethyleneoxy adducts thereof, such as polyglyceric acid fatty acid esters or polyethylene sorbitan fatty esters (Tweens), and furthermore polyoxyethylene fatty alcohol ethers or polyoxyethylene fatty acid esters, or corresponding ionic emulsifiers, such as alkali metal salts of fatty alcohol sulfates, for example, sodium lauryl sulfate, sodium cetyl sulfate or sodium stearyl sulfate, which are usually used in the presence of fatty alcohols, for example cetyl stearyl alcohol or stearyl alcohol. Additives to the aqueous phase are, inter alia, agents which prevent the creams from drying out, for example polyalcohols, such as glycerol, sorbitol, propylene glycol and/or polyethylene glycols, and furthermore preservatives and odoriferous substances.

Pastes are creams and ointments having secretion-absorbing powder constituents, such as metal oxides, for example, titanium oxide or zinc oxide, and furthermore talc and/or aluminium silicates, which have the task of binding the moisture or secretions present.

Foams (i.e., liquid oil-in-water emulsions packaged in aerosol form) can be administered from pressurized containers. Propellant gases include halogenated hydrocarbons, such as polyhalogenated alkanes such as dichlorofluoromethane and dichlorotetrafluoroethane, or, preferably, non-halogenated gaseous hydrocarbons, air, $N_2O$, or carbon dioxide. The oily phases used are, inter alia, those mentioned above for ointments and creams, and the additives mentioned there are likewise used.

Tinctures and solutions usually comprise an aqueous-ethanolic base to which, humectants for reducing evaporation, such as polyalcohols (e.g., glycerol, glycols, polyethylene glycol) and re-oiling substances, such as fatty acid esters with lower polyethylene glycols (e.g., lipophilic substances soluble in the aqueous mixture) to substitute the fatty substances removed from the skin with the ethanol, and, if necessary or desired, other excipients and additives, are admixed.

The present invention further provides veterinary compositions comprising at least one active ingredient as above defined together with a veterinary carrier therefor. Veterinary carriers are materials for administering the composition and may be solid, liquid, or gaseous materials, which are inert or acceptable in the veterinary art and are compatible with the active ingredient. These veterinary compositions may be administered orally, parenterally, or by any other desired route.

The invention also relates to a process or method for treatment of the disease states mentioned above. The compounds can be administered prophylactically or therapeutically as such or in the form of pharmaceutical compositions, preferably in an amount, which is effective against the diseases mentioned. With a warm-blooded animal, for example, a human requiring such treatment, the compounds are used, in particular, in the form of pharmaceutical composition. A daily dose of about 0.1 to about 5 g, preferably 0.5 g to about 2 g, of a compound of the present invention is administered here for a body weight of about 70 kg.

*, #P<0.05; , ##P<0.01; *, ###P<0.001; *P compared with vehicle with 800 μM salsolinol, #P compared with vehicle without salsolinol. A value of P<0.05 is considered statistically significant.

Figure 1:
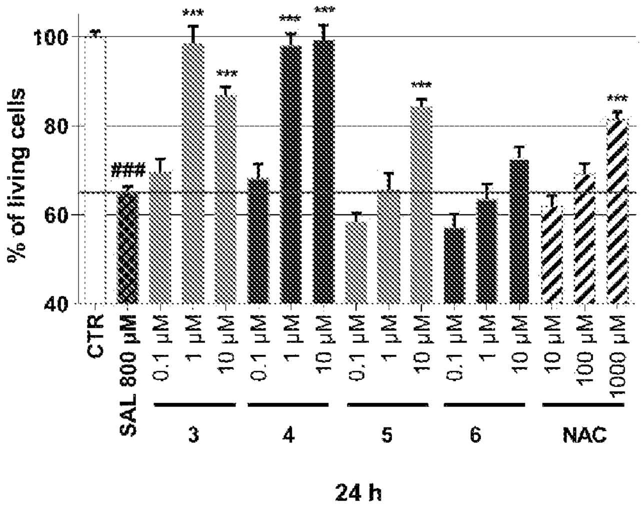
FIG. 1 shows neuroprotective effect of novel compounds in salsolinol-induced model of Parkinson's disease. Along with the compounds of the invention at 0.1, 1 and 10 μM N-acetyl cysteine (NAC, at 10, 100 and 1000 μM)) was used as positive control. All results are presented as mean±the standard error of the mean (SEM) in triplicate experiments (n=3) in three separated days. ANOVA, Tukey post hoc test.
Figure 2:
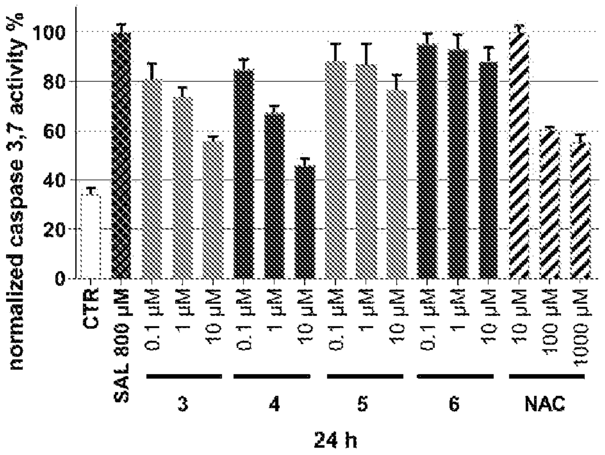

FIG. 2 shows the protective effects of novel compounds after salsolinol-induced caspase-3,7 activity. Examples were tested in active compound concentrations along with positive control N-acetyl cysteine. All results are present mean±the standard error of the mean (SEM) in triplicate experiments in at least two separated days.

Figure 3:
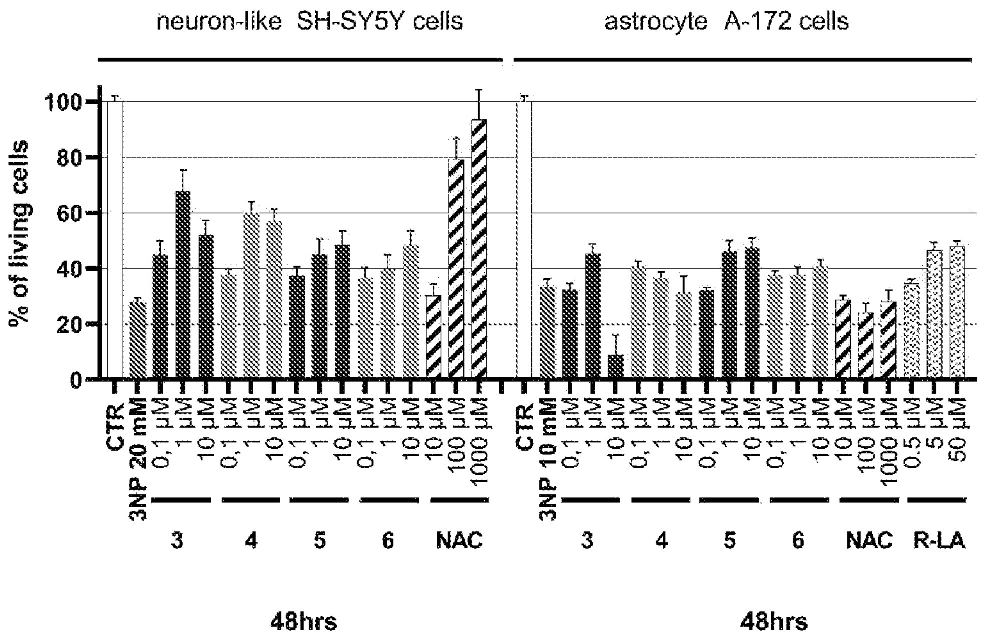

FIG. 3 depicts neuroprotective and astroprotective effect of novel compounds in 3-nitropropionic acid (3NPA)-induced model of Huntington's disease. Along with the compounds of the invention at 0.1, 1 and 10 μM N-acetyl cysteine (NAC, at 10, 100 and 1000 μM) and R-lipoic acid (R-LA, at 0.5, 5 and 50 μM) was used as positive control. All results are presented as mean±the standard error of the mean (SEM) in triplicate experiments (n=3) in at least three separated days.

Figure 4:
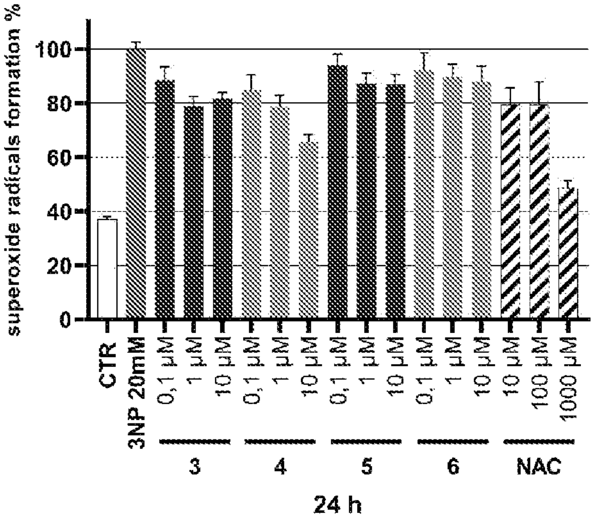

FIG. 4 depicts neuroprotective and astroprotective effect of novel compounds in 3-nitropropionic acid (3NPA)-induced model of Huntington's disease on neuron-like SH-SY5Y and astrocyte A-172 cells. Along with the compounds of the invention at 0.1, 1 and 10 μM N-acetyl cysteine (NAC, at 10, 100 and 1000 μM) and R-Lipoic acid (R-LA, at 0.5, 5 and 50 μM) was used as positive control. All results are presented as mean±the standard error of the mean (SEM) in triplicate experiments (n=3) in three (SH-SY5Y) and five (A-172) separated days.

EXAMPLES OF CARRYING OUT THE INVENTION

The following examples serve to illustrate the invention without limiting the scope thereof. Unless otherwise stated, all percentages and the like amounts are based on weight. The starting materials may be obtained from commercial sources (Sigma, Aldrich, Fluka, etc.) or can be prepared as described below.

Melting points were determined using either the Büchi B-545 apparatus or the STUART SMP30 apparatus and are uncorrected. Infrared spectra were recorded on a Nicolet Avatar 370 FTIR and processed in the OMNIC 9.8.372. DRIFT stands for Diffuse Reflectance Infrared Fourier Transform. $^1$H and $^{13}$C experiments were performed on Jeol ECX-500SS (500 MHz for $^1$H), and Varian$^{UNITY}$ Inova 400 (400 MHz for $^1$H) instruments, using $CDCl_3$, DMSO-$d_6$, $CD_3OD$ or THF-$d_8$ as solvents (25° C.). Chemical shifts (δ) were referenced to the residual signal of the solvent ($CDCl_3$, DMSO-$d_6$, $CD_3OD$ or THF-$d_8$) and are reported in parts per million (ppm). Coupling constants (J) are reported in Hertz (Hz). NMR spectra were processed in the ACD/NMR Processor Academic Edition 12.01, MestReNova 6.0.2-5475 or JEOL Delta v5.0.5.1. HRMS analysis was performed using an LC-MS Orbitrap Elite high-resolution mass spectrometer with electrospray ionization (Dionex Ultimate 3000, Thermo Exactive plus, MA, USA). Spectra were taken at the positive and negative mode in the range of 100-1000 m/z. The samples were dissolved in MeOH and injected to the mass spectrometer over autosampler after HPLC separation: precolumn Phenomenex Gemini (C18, 50×2 mm, 2.6 μm), mobile phase isocratic MeOH/water/HCOOH 95:5:0.1. The course of the reactions was monitored by TLC on Kieselgel 60 $F_{254}$ plates (Merck) detected first by UV light (254 nm) and then by spraying with 10% aqueous $H_2SO_4$ and heating to 150° C.-200° C. Purification was performed using column chromatography on Silica gel 60 (Merck 7734).

Starting propargyl derivatives were prepared from starting commercially available lupane derivatives according to the following scheme:

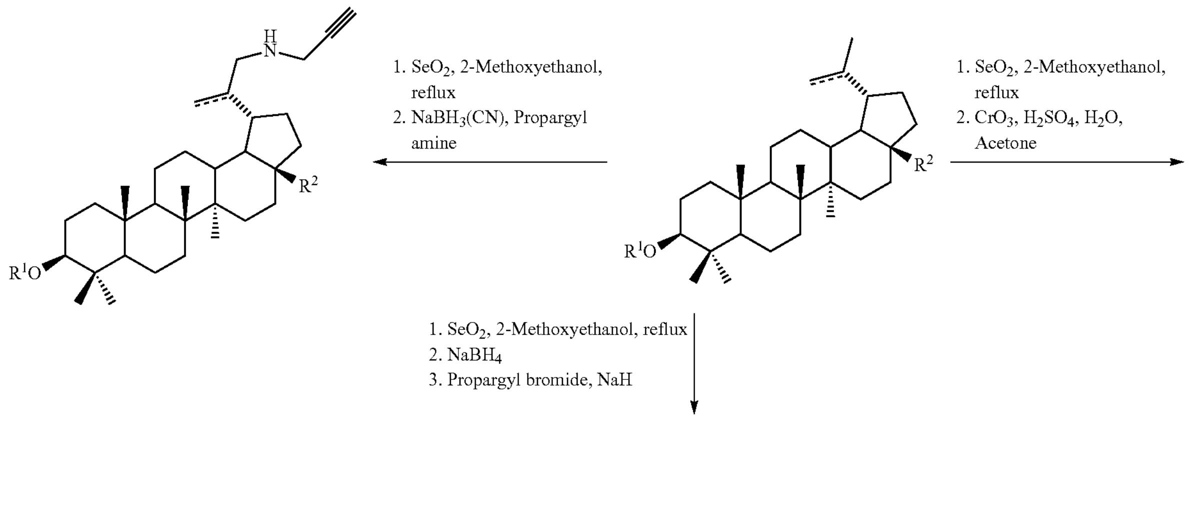

-continued
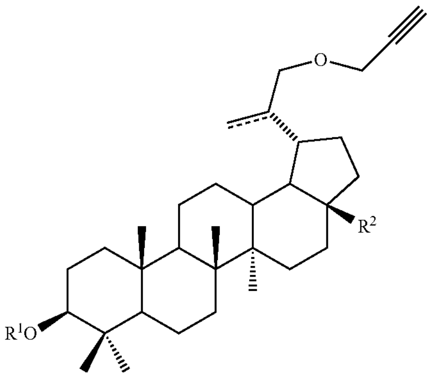
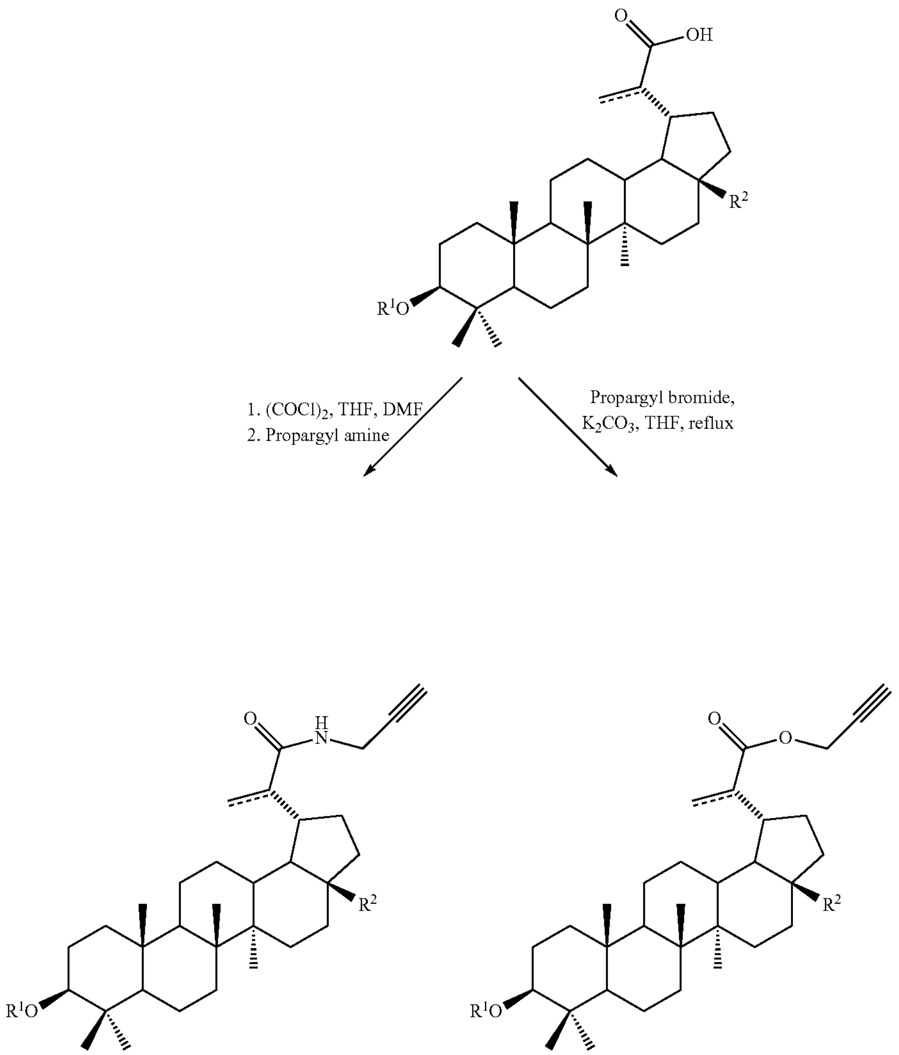

Synthesis of Substituted Triazole Conjugates

Some of the protected molecules are available according to the following reaction scheme:

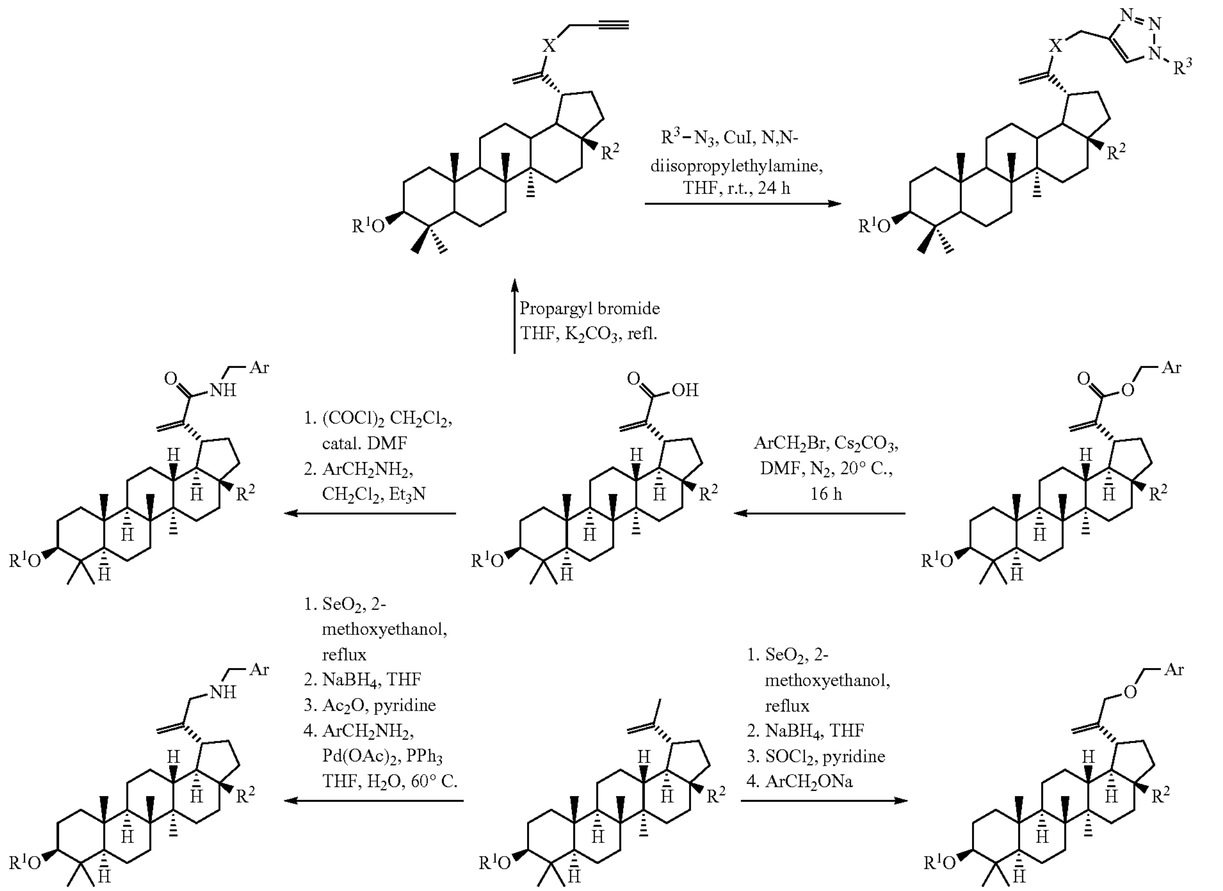

Ar: Aromatic cycle, e.g. pyridine, pyrimidine, pyrrole, isoxazole, thiofene, furane, imidazole, thiazole, benzene, etc.

A) Huisgen Cycloaddition

Each azide (0.34 mmol), CuI (3.3 mg, 0.017 mmol), and N,N-diisopropylethylamine (22 mg, 0.17 mmol) were added to a solution of the propargylated terpene (0.17 mmol) in THF (5 mL). Colourless solution changed immediately into brown-green which is a sign of the cycloaddition reaction. The reaction mixture was stirred at r.t. for another 24 h and then the THF was evaporated under reduced pressure. Chromatography on silica gel (5 g, cyclohexane/EtOAc 3:1) afforded pure triazole conjugate which was then crystallized from chloroform and methanol to give white colourless crystals of the final product with average yield 74%.

Example 1

(1-[galactos-1-yl]-1H-1,2,3-triazol-4-yl)-methoxy-lup-20(29)-en-3,28-diol diacetate (Compound 1)

Prepared from 1-Azido-2,3,4,6-tetraacetyl-β-D-galactopyranose (127 mg, 0.34 mmol) and 30-propargyloxylup-20(29)-en-3,28-diol diacetate (100 mg, 0.17 mmol). White solid, chemical formula: $C_{51}R_{75}N_3O_{14}$, yield (%): 90 mg, 55%. Mp: 120-126° C. (cyclohexane/EtOAc); IR ν ($cm^{-1}$): 1751 (C═O), 1628 (C═C). $^1H$ NMR ($CDCl_3$, 500 MHz) δ, ppm: 0.83 (3H, s); 0.84 (6H, s); 0.93 (3H, s); 1.02 (3H, s, 5×$CH_3$); 1.88 (3H, s); 2.01 (3H, s); 2.04 (3H, s); 2.05 (3H, s); 2.06 (3H, s); 2.23 (3H, s, 6×Ac); 2.77 (1H, td, $J_1$=11.2 Hz, $J_2$=5.2 Hz, H-19β); 3.85 (1H, d, J=11.2 Hz); 4.10-4.30 (4H, m); 4.46 (1H, dd, $J_1$=10.0 Hz, $J_2$=6.0 Hz, H-3α); 5.20-5.35 (3H, m); 5.50-5.65 (3H, m, 5×H—$CH_2O$, 1×H-29 pro E); 5.85 (1H, d, J=9.1 Hz, 1×H—$CH_2O$); 6.12 (1H, bs, H-29 pro Z); 7.93 (1H, s triazole). $^{13}C$ NMR ($CDCl_3$, 500 MHz) δ, ppm: 14.58; 15.98; 16.08; 16.45; 18.11; 20.18; 20.25; 20.45; 20.60; 20.65; 20.80; 20.99; 21.28; 23.64; 26.88; 26.96; 27.32; 27.90; 29.74; 30.89; 34.09; 34.19; 37.01; 37.16; 37.75; 38.35; 40.82; 42.59; 46.41; 50.05; 55.32; 57.58; 61.09; 62.55; 66.78; 67.82; 70.71; 74.11; 80.85; 86.31; 119.89; 122.31; 143.46; 145.98; 166.92; 168.93; 169.75; 169.93; 170.25; 170.97; 171.47. HRMS (ESI): m/z calcd for $C_{51}H_{75}N_3O_{14}$ $[M+H]^+$ 954.5322, found 953.5324.

Example 2

(1-[glucos-1-yl]-1H-1,2,3-triazol-4-yl)-methoxylup-20(29)-en-3,28-diol diacetate (Compound 2)

It was prepared from 1-Azido-2,3,4,6-tetraacetyl-β-D-glucopyranose (127 mg, 0.34 mmol) and diacetate (100 mg, 0.17 mmol). White solid, chemical formula: $C_{51}H_{75}N_3O_{14}$, yield (%): 121 mg, 74%. Mp: 122-126° C. (cyklohexane/EtOAc); IR ν ($cm^{-1}$): 1732 (C═O); 1635 (C═C). $^1$H NMR ($CDCl_3$, 500 MHz) δ, ppm: 0.82 (3H, s); 0.83 (6H, s); 0.92 (3H, s); 1.02 (3H, s, 5×$CH_3$); 1.85 (3H, s); 2.02 (3H, s); 2.03 (3H, s); 2.06 (3H, s); 2.08 (3H, s); 2.16 (3H, s, 6×Ac); 2.76 (1H, td $J_1$=11.5 Hz, $J_2$=5.8 Hz, H-19β); 3.86 (1H, td, J=10.8 Hz); 3.98-4.05 (1H, m); 4.09-4.35 (4H, m); 4.41 (1H, dd, $J_1$=10.1 Hz, $J_2$=5.2 Hz, H-3α); 5.20-5.35 (3H, m); 5.42 (2H, m); 5.58 (1H, m); 5.87 (1H, d, J=9.2 Hz); 6.11 (1H, s); 7.85 (1H, s, triazole). $^{13}$C NMR ($CDCl_3$, 500 MHz) δ, ppm: 14.75; 16.14; 16.25; 16.62; 18.12; 20.08; 20.50; 20.65; 20.69; 20.80; 20.99; 21.28; 23.64; 26.88; 26.96; 27.37; 27.91; 29.74; 34.09; 34.17; 37.01; 37.16; 37.75; 38.34; 40.82; 42.59; 46.41; 50.04; 55.32; 57.67; 61.48; 62.53; 67.64; 70.24; 73.23; 75.38; 81.00; 85.93; 122.20; 122.25; 143.65; 143.81; 167.03; 168.91; 169.45; 170.02; 170.58; 171.12; 171.63. HRMS (ESI): m/z calcd for $C_{51}H_{73}N_3O_{15}$ $[M+H]^+$ 968.5114, found 968.5131.

Example 3

Pyridin-4-yl-methyl 3β,28-bis(acetyloxy)lup-20(30)-en-29-oate (Compound 3)

3,28-Bis(acetyloxy)lup-20(29)-en-30-oic acid (50 mg, 0.09 mmol) was dissolved in dry DMF (2.5 mL). $Cs_2CO_3$ (88 mg, 0.27 mmol) was added to the reaction mixture followed by an alkyl bromide (0.14 mmol) at room temperature under nitrogen atmosphere. After 16 h of stirring the reaction mixture was diluted with water, extracted with dichloromethane and organic layer was washed with water and dried over $Na_2SO_4$, solvent was evaporated in vacuum. The residue was purified by column chromatography on $SiO_2$ eluting with hexane/EtOAc. Pyridin-4-yl-methyl 3β,28-bis(acetyloxy)lup-20(30)-en-29-oate was obtained as a white solid; (hexane/EtOAc); $R_f$ 0.14 (silica gel, hexane/EtOAc, 3:2). $^1$H NMR ($CDCl_3$, 500 MHz) δ, ppm: 0.83 s (3H, Me), 0.837 s (3H, Me), 0.841 s (3H, Me), 0.91 s (3H, Me), 1.02 s (3H, Me), 2.04 s (3H, AcO), 2.07 s (3H, AcO), 2.14-2.22 m (1H), 2.80 td (1H, $J_1$=11.3 Hz, $J_2$=5.5 Hz, H-19), 3.86 d (1H, J=11.0 Hz, H-28a), 4.26 dd (1H, $J_1$=11.0 Hz, $J_2$=1.1 Hz, H-28b), 4.46 dd (1H, $J_1$=10.7 Hz, $J_2$=5.3 Hz, H-3), 5.19 d (1H, J=13.7 Hz, $CH_a$ pyridinyl), 5.24 d (1H, J=13.7 Hz, $CH_b$ pyridinyl), 5.65 s (1H, H-30a), 6.20 s (1H, H-30b), 7.26 d ($2H_{Ar}$, J=6.0 Hz), 8.61 d ($2H_{Ar}$, J=6.0 Hz). $^{13}$C NMR ($CDCl_3$, 125 MHz) δ, ppm: 14.7, 16.1, 16.2, 16.6, 18.3, 21.0, 21.1, 21.4, 23.8, 27.1, 27.5, 28.1, 29.8, 29.9, 32.4, 34.3, 34.4, 37.2, 37.3, 37.9, 38.5, 41.0, 42.8, 46.6, 50.2, 51.4, 55.5, 62.7, 64.6, 81.0, 122.0, 124.3, 145.2, 146.3, 150.2, 166.8, 171.1, 171.6. HRMS (ESI): $C_{40}H_{58}NO_6$ found 648.4256 $[M+H]^+$; calcd. 648.4259.

Example 4

Pyridin-3-yl-methyl (3β)-3,28-bis(acetyloxy)lup-20(30)-en-29-oate (Compound 4)

It was prepared according to the same procedure and it was obtained (31 mg; 53%) as a white solid; $R_f$ 0.18 (silica gel, hexane/EtOAc, 3:2).

$^1$H NMR ($CDCl_3$, 500 MHz) δ, ppm: 0.83 s (6H, 2Me), 0.84 s (3H, Me), 0.88 s (3H, Me), 1.01 s (3H, Me), 2.04 s (3H, AcO), 2.06 s (3H, AcO), 2.10-2.19 m (1H), 2.76 td (1H, $J_1$=11.3 Hz, $J_2$=5.6 Hz, H-19), 3.84 d (1H, J=11.0 Hz, H-28a), 4.25 dd (1H, $J_1$=11.0 Hz, $J_2$=0.8 Hz, H-28b), 4.46 dd (1H, $J_1$=11.1 Hz, $J_2$=5.0 Hz, H-3), 5.20 d (1H, J=12.7 Hz, $CH_a$ pyridinyl), 5.24 d (1H, J=12.7 Hz, $CH_b$ pyridinyl), 5.60 s (1H, H-30a), 6.12 s (1H, H-30b), 7.31 ddd ($1H_{Ar}$, $J_1$=7.8 Hz, $J_2$=4.7 Hz, $J_3$=0.6 Hz), 7.70-7.72 m ($1H_{Ar}$), 8.59 dd ($1H_{Ar}$, $J_1$=4.7 Hz, $J_2$=1.4 Hz), 8.65 d ($1H_{Ar}$, $J_1$=1.4 Hz).

$^{13}$C NMR ($CDCl_3$, 125 MHz) δ, ppm: 14.7, 16.1, 16.2, 16.6, 18.3, 20.9, 21.1, 21.4, 23.8, 27.1, 27.4, 28.1, 29.8, 29.9, 32.2, 34.2, 34.4, 37.2, 37.3, 37.9, 38.5, 41.0, 42.7, 46.6, 50.2, 51.2, 55.5, 62.7, 64.0, 81.0, 123.6, 124.1, 131.9, 136.1, 146.4, 149.8, 149.9, 167.0, 171.1, 171.6.

HRMS (ESI): $C_{40}H_{58}NO_6$ found 648.4258 $[M+H]^+$; calcd. 648.4259.

Example 5

Furan-2-yl-methyl 3β,28-diacetyloxylup-20(29)-en-30-oate (Compound 5)

It was prepared according to the general procedure from 3,28-bis(acetyloxy)lup-20(29)-en-30-oic acid (50 mg; 0.09 mmol), $Ph_3P$ (34 mg, 0.13 mmol), furfuryl alcohol (8 μL, 9 mg, 0.09 mmol) and DIAD (27 μL, 28 mg, 0.14 mmol) in $CH_2Cl_2$ (2 mL). After purification (mobile phase hexane/EtOAc 5:1) compound # (46 mg; 81%) was obtained as a white solid; (hexane/EtOAc); $R_f$ 0.41 (silica gel, hexane/EtOAc, 4:1). $^1$H NMR ($CDCl_3$, 500 MHz) δ, ppm: 0.82 s (6H, 2Me), 0.84 s (3H, Me), 0.89 s (3H, Me), 1.01 s (3H, Me), 1.75-1.90 m (3H), 2.04 s (3H, AcO), 2.06 s (3H, AcO), 2.09-2.17 m (1H), 2.74 td (1H, $J_1$=11.3 Hz, $J_2$=5.7 Hz, H-19), 3.84 d (1H, J=11.0 Hz, H-28a), 4.25 dd (1H, $J_1$=11.0 Hz, $J_2$=1.3 Hz, H-28b), 4.46 dd (1H, $J_1$=10.9 Hz, $J_2$=5.3 Hz, H-3), 5.13 d (1H, J=13.1 Hz, $CH_a$ furanyl), 5.16 d (1H, J=13.1 Hz, $CH_b$ furanyl), 5.55 s (1H, H-30a), 6.08 s (1H, H-30b), 6.37 dd (1H, $J_1$=3.3 Hz, $J_2$=1.9 Hz, H-4'), 6.42 dd (1H, $J_1$=3.3 Hz, $J_2$=0.8 Hz, H-3'), 7.42 dd (1H, $J_1$=1.9 Hz, $J_2$=0.8 Hz, H-5'). $^{13}$C NMR ($CDCl_3$, 125 MHz) δ, ppm: 14.7, 16.1, 16.2, 16.6, 18.3, 20.9, 21.2, 21.4, 23.8, 27.1, 27.2, 28.1, 29.8, 29.9, 32.0, 34.26, 34.33, 37.2, 37.3, 37.9, 38.5, 41.0, 42.8, 46.5, 50.2, 51.0, 55.5, 58.3, 62.8, 81.0, 110.70, 110.74, 124.2, 143.3, 146.3, 149.7, 167.0, 171.1, 171.7. HRMS (ESI): $C_{39}H_{57}O_7$ found 637.4095 $[M+H]^+$; calcd. 637.4099.

Example 6

Thiophen-2-ylmethyl 3β,28-diacetyloxy-lup-20(29)-en-30-oate (Compound 6)

It was prepared according to the general procedure from 3,28-bis(acetyloxy)lup-20(29)-en-30-oic acid (50 mg; 0.09 mmol), $Ph_3P$ (34 mg, 0.13 mmol), 2-thiophenemethanol (10 mg, 0.09 mmol) and DIAD (27 μL, 28 mg, 0.14 mmol) in $CH_2Cl_2$ (2 mL). After purification (mobile phase hexane/EtOAc 8:1) compound # (52 mg; 88%) was obtained as a white solid; $R_f$ 0.23 (silica gel, hexane/EtOAc, 6:1). $^1$H NMR ($CDCl_3$, 500 MHz) δ, ppm: 0.83 s (6H, 2Me), 0.84 s (3H, Me), 0.87 s (3H, Me), 1.01 s (3H, Me), 1.75-1.93 m (3H), 2.04 s (3H, AcO), 2.06 s (3H, AcO), 2.09-2.18 m (1H), 2.75 td (1H, $J_1$=11.5 Hz, $J_2$=5.9 Hz, H-19), 3.84 d (1H, J=11.0 Hz, H-28a), 4.25 dd (1H, $J_1$=11.0 Hz, $J_2$=0.9 Hz, H-28b), 4.46 dd (1H, $J_1$=10.9 Hz, $J_2$=5.2 Hz, H-3), 5.34 dd (1H, $J_1$=12.9 Hz, $J_2$=0.6 Hz, $CH_a$ thienyl), 5.37 d (1H, $J_1$=12.9 Hz, $J_2$=0.6 Hz, $CH_b$ thienyl), 5.56 s (1H, H-30a), 6.10 s (1H, H-30b), 6.99 dd (1H, $J_1$=5.1 Hz, $J_2$=3.5 Hz, H-4'), 7.41 ddt (1H, $J_1$=3.5 Hz, $J_2$=1.2 Hz, $J_3$=0.6 Hz, H-3'), 7.32 dd (1H, $J_1$=5.1 Hz, $J_2$=1.2 Hz, H-5'). $^{13}$C NMR ($CDCl_3$, 125 MHz) δ, ppm: 14.7, 16.1, 16.2, 16.6, 18.3, 20.9, 21.2, 21.4, 23.8, 27.1, 27.3, 28.1, 29.8, 29.9, 32.0, 34.3, 34.4, 37.2, 37.3, 37.9, 38.5, 41.0, 42.8, 46.6, 50.2, 51.1, 55.5, 60.8, 62.8, 81.0, 124.1, 126.91, 126.92, 128.2, 138.2, 146.4, 167.1, 171.1, 171.7. HRMS (ESI): $C_{39}H_{57}O_6S$ found 653.3870 $[M+H]^+$; calcd. 653.3870.

TABLE 1

Prepared terpenes of the general formula I, where A = B = Y = N, m = 1 and ------ is double bond (Ac = acetyl)

| | Substituents | | | | CHN analysis | MS analysis |
|---|---|---|---|---|---|---|
| | X | $R^1$ | $R^2$ | $R^3$ | [% C, % H, % N] [calculated/found] | $[M + H]^+$ |
| 7 | $CH_2O$ | Ac | $CH_2OAc$ | H | 71.23/71.15, 9.21/9.27, 6.74/6.70 | 624 |
| 8 | $CH_2O$ | Ac | $CH_2OAc$ | $CH_3$ | 71.55/71.31, 9.32/9.21, 6.59/6.74 | 638 |
| 9 | $CH_2O$ | Ac | $CH_2OAc$ | pyridin-3-yl | 71.97/71.64, 8.63/8.53, 7.99/8.11 | 701 |
| 10 | $CH_2O$ | Ac | $CH_2OAc$ | peracetylgalactosyl | 64.20/64.02, 7.92/7.54, 4.40/4.14 | 954 |
| 11 | $CH_2O$ | Ac | $CH_2OAc$ | peracetylglucosyl | 64.20/64.13, 7.92/7.71, 4.40/4.24 | 954 |
| 12 | $CH_2O$ | Ac | $CH_2OAc$ | galactosyl | 65.71/65.70, 8.59/8.47, 5.35/5.15 | 786 |
| 13 | $CH_2O$ | Ac | $CH_2OAc$ | glucosyl | 65.71/65.65, 8.59/8.50, 5.35/5.28 | 786 |
| 14 | $CH_2O$ | H | $CH_2OH$ | H | 73.43/73.40, 9.90/10.00, 7.78/7.81 | 540 |
| 15 | $CH_2O$ | H | $CH_2OH$ | $CH_3$ | 73.74/73.70, 10.01/10.02, 7.59/7.47 | 554 |
| 16 | $CH_2O$ | H | $CH_2OH$ | pyridin-3-yl | 73.99/74.14, 9.15/9.24, 9.08/9.14 | 617 |
| 17 | $CH_2O$ | H | $CH_2OH$ | peracetylgalactosyl | 64.88/64.37, 8.23/8.24, 4.83/4.72 | 913 |
| 18 | $CH_2O$ | H | $CH_2OH$ | peracetylglucosyl | 64.88/64.66, 8.23/8.08, 4.83/4.55 | 913 |
| 19 | $CH_2O$ | H | $CH_2OH$ | galactosyl | 66.19/66.17, 8.81/8.74, 5.65/5.41 | 744 |
| 20 | $CH_2O$ | H | $CH_2OH$ | glucosyl | 66.19/66.02, 8.81/9.03, 5.65/5.81 | 744 |
| 21 | $CH_2NH$ | Ac | $CH_2OAc$ | H | 71.35/71.28, 9.39/9.47, 8.99/9.07 | 623 |
| 22 | $CH_2NH$ | Ac | $CH_2OAc$ | $CH_3$ | 71.66/71.59, 9.50/9.47, 8.80/8.46 | 637 |
| 23 | $CH_2NH$ | Ac | $CH_2OAc$ | pyridin-3-yl | 72.07/72.35, 8.78/8.69, 10.01/9.87 | 699 |
| 24 | $CH_2NH$ | Ac | $CH_2OAc$ | peracetylgalactosyl | 64.26/64.23, 8.04/7.85, 5.88/5.92 | 954 |
| 25 | $CH_2NH$ | Ac | $CH_2OAc$ | peracetylglucosyl | 64.26/64.15, 8.04/7.96, 5.88/5.48 | 954 |
| 26 | $CH_2NH$ | Ac | $CH_2OAc$ | galactosyl | 65.79/65.71, 8.73/8.77, 7.14/7.01 | 786 |
| 27 | $CH_2NH$ | Ac | $CH_2OAc$ | glucosyl | 65.79/65.68, 8.73/8.67, 7.14/7.21 | 786 |
| 28 | $CH_2NH$ | H | $CH_2OH$ | H | 73.56/73.47, 10.10/10.05, 10.40/10.27 | 539 |
| 29 | $CH_2NH$ | H | $CH_2OH$ | $CH_3$ | 73.87/73.88, 10.21/10.28, 10.13/10.02 | 553 |
| 30 | $CH_2NH$ | H | $CH_2OH$ | pyridin-3-yl | 74.11/74.27, 9.33/9.27, 11.37/11.33 | 616 |
| 31 | $CH_2NH$ | H | $CH_2OH$ | peracetylgalactosyl | 64.95/64.49, 8.35/8.17, 6.45/6.37 | 870 |
| 32 | $CH_2NH$ | H | $CH_2OH$ | peracetylglucosyl | 64.95/64.73, 8.35/8.54, 6.45/6.54 | 870 |
| 33 | $CH_2NH$ | H | $CH_2OH$ | galactosyl | 66.83/66.95, 9.20/9.13, 7.99/7.75 | 701 |
| 34 | $CH_2NH$ | H | $CH_2OH$ | glucosyl | 66.83/66.68, 9.20/9.21, 7.99/8.20 | 701 |
| 35 | CONH | Ac | $CH_2OAc$ | H | 69.78/69.65, 8.86/8.95, 8.80/8.67 | 637 |
| 36 | CONH | Ac | $CH_2OAc$ | $CH_3$ | 70.12/70.24, 8.98/9.04, 8.61/8.57 | 651 |
| 37 | CONH | Ac | $CH_2OAc$ | pyridin-3-yl | 70.66/70.58, 8.33/8.17, 9.81/9.98 | 714 |
| 38 | CONH | Ac | $CH_2OAc$ | peracetylgalactosyl | 63.34/63.27, 7.71/7.57, 5.79/5.81 | 968 |
| 39 | CONH | Ac | $CH_2OAc$ | peracetylglucosyl | 63.34/63.54, 7.71/7.68, 5.79/5.71 | 968 |
| 40 | CONH | Ac | $CH_2OAc$ | galactosyl | 64.64/64.71, 8.33/8.21, 7.01/7.14 | 799 |
| 41 | CONH | Ac | $CH_2OAc$ | glucosyl | 64.64/64.57, 8.33/8.38, 7.01/6.94 | 799 |
| 42 | CONH | H | $CH_2OH$ | H | 71.70/71.50, 9.48/9.39, 10.14/9.99 | 553 |
| 43 | CONH | H | $CH_2OH$ | $CH_3$ | 72.05/72.13, 9.60/9.38, 9.88/10.03 | 567 |
| 44 | CONH | H | $CH_2OH$ | pyridin-3-yl | 72.46/72.27, 8.80/8.79, 11.12/11.07 | 629 |
| 45 | CONH | H | $CH_2OH$ | peracetylgalactosyl | 63.92/63.71, 7.99/7.78, 6.34/6.14 | 884 |
| 46 | CONH | H | $CH_2OH$ | peracetylglucosyl | 63.92/63.64, 7.99/7.78, 6.34/6.25 | 884 |
| 47 | CONH | H | $CH_2OH$ | galactosyl | 65.52/65.27, 8.74/8.57, 7.84/8.02 | 715 |
| 48 | CONH | H | $CH_2OH$ | glucosyl | 65.52/65.79, 8.74/8.71, 7.84/7.77 | 715 |
| 49 | $CH_2O$ | Ac | COOH | H | 70.56/70.47, 8.97/9.14, 7.05/6.91 | 596 |
| 50 | $CH_2O$ | Ac | COOH | $CH_3$ | 70.90/80.02, 9.09/8.94, 6.89/6.78 | 610 |
| 51 | $CH_2O$ | Ac | COOH | pyridin-3-yl | 71.40/71.34, 8.39/8.27, 8.33/8.27 | 673 |
| 52 | $CH_2O$ | Ac | COOH | peracetylgalactosyl | 63.55/63.27, 7.73/7.57, 4.54/4.36 | 927 |
| 53 | $CH_2O$ | Ac | COOH | peracetylglucosyl | 63.55/63.64, 7.73/7.55, 4.54/4.23 | 927 |
| 54 | $CH_2O$ | Ac | COOH | galactosyl | 64.97/64.97, 8.38/8.24, 5.54/5.47 | 758 |
| 55 | $CH_2O$ | Ac | COOH | glucosyl | 64.97/64.78, 8.38/8.27, 5.54/5.39 | 758 |
| 56 | $CH_2O$ | H | COOH | H | 71.57/71.69, 9.28/9.34, 7.59/7.47 | 554 |
| 57 | $CH_2O$ | H | COOH | $CH_3$ | 71.92/72.07, 9.41/9.37, 7.40/7.65 | 568 |
| 58 | $CH_2O$ | H | COOH | pyridin-3-yl | 72.35/72.29, 8.63/8.55, 8.88/9.00 | 631 |
| 59 | $CH_2O$ | H | COOH | peracetylgalactosyl | 63.85/63.77, 7.87/7.69, 4.75/4.71 | 884 |
| 60 | $CH_2O$ | H | COOH | peracetylglucosyl | 63.85/63.68, 7.87/7.74, 4.75/4.59 | 884 |
| 61 | $CH_2O$ | H | COOH | galactosyl | 64.97/64.79, 8.38/8.17, 5.54/5.47 | 758 |
| 62 | $CH_2O$ | H | COOH | glucosyl | 64.97/64.88, 8.38/8.34, 5.54/5.41 | 758 |
| 63 | $CH_2NH$ | Ac | COOH | H | 70.55/70.39, 9.30/9.24, 9.40/9.57 | 595 |
| 64 | $CH_2NH$ | Ac | COOH | $CH_3$ | 71.02/70.87, 9.27/9.15, 9.20/9.03 | 609 |
| 65 | $CH_2NH$ | Ac | COOH | pyridin-3-yl | 71.50/71.38, 8.55/8.64, 10.42/10.47 | 672 |
| 66 | $CH_2NH$ | Ac | COOH | peracetylgalactosyl | 63.62/63.27, 7.84/7.77, 6.06/6.01 | 926 |
| 67 | $CH_2NH$ | Ac | COOH | peracetylglucosyl | 63.62/63.51, 7.84/7.57, 6.06/5.79 | 926 |
| 68 | $CH_2NH$ | Ac | COOH | galactosyl | 65.05/65.17, 8.52/8.24, 7.40/7.51 | 757 |
| 69 | $CH_2NH$ | Ac | COOH | glucosyl | 65.05/64.87, 8.52/8.48, 7.40/7.32 | 757 |
| 70 | $CH_2NH$ | H | COOH | H | 71.70/71.54, 9.48/9.57, 10.14/10.03 | 553 |
| 71 | $CH_2NH$ | H | COOH | $CH_3$ | 72.05/71.92, 9.60/9.67, 9.88/9.74 | 567 |
| 72 | $CH_2NH$ | H | COOH | pyridin-3-yl | 72.46/72.39, 8.80/8.69, 11.12/11.04 | 630 |
| 73 | $CH_2NH$ | H | COOH | peracetylgalactosyl | 63.92/63.78, 7.99/7.74, 6.34/6.34 | 884 |
| 74 | $CH_2NH$ | H | COOH | peracetylglucosyl | 63.92/63.79, 7.99/7.71, 6.34/6.28 | 884 |
| 75 | $CH_2NH$ | H | COOH | galactosyl | 65.52/65.71, 8.74/8.71, 7.84/7.88 | 715 |
| 76 | $CH_2NH$ | H | COOH | glucosyl | 65.52/65.27, 8.74/8.68, 7.84/7.70 | 715 |
| 77 | CONH | Ac | COOH | H | 69.05/69.21, 8.61/8.54, 9.20/9.07 | 609 |
| 78 | CONH | Ac | COOH | $CH_3$ | 69.42/69.37, 8.74/8.56, 9.00/8.87 | 623 |
| 79 | CONH | Ac | COOH | Pyridin-3-yl | 70.04/69.95, 8.08/7.87, 10.21/10.17 | 686 |

TABLE 1-continued

Prepared terpenes of the general formula I, where
A = B = Y = N, m = 1 and ------ is double bond (Ac = acetyl)

| | Substituents | | | | CHN analysis | MS analysis |
|---|---|---|---|---|---|---|
| | X | $R^1$ | $R^2$ | $R^3$ | [% C, % H, % N] [calculated/found] | $[M + H]^+$ |
| 80 | CONH | Ac | COOH | peracetylgalactosyl | 62.67/62.57, 7.51/7.13, 5.97/5.76 | 939 |
| 81 | CONH | Ac | COOH | peracetylglucosyl | 62.67/62.76, 7.51/7.68, 5.97/5.47 | 939 |
| 82 | CONH | Ac | COOH | galactosyl | 63.87/63.74, 8.11/7.95, 7.27/7.10 | 771 |
| 83 | CONH | Ac | COOH | glucosyl | 63.87/63.81, 8.11/8.20, 7.27/7.14 | 771 |
| 84 | CONH | H | COOH | H | 69.93/70.05, 8.89/8.76, 9.89/9.99 | 567 |
| 85 | CONH | H | COOH | $CH_3$ | 70.31/70.27, 9.02/8.88, 9.65/9.74 | 581 |
| 86 | CONH | H | COOH | pyridin-3-yl | 70.89/70.78, 8.30/8.17, 10.88/10.97 | 644 |
| 87 | CONH | H | COOH | peracetylgalactosyl | 62.93/62.74, 7.64/7.71, 6.25/6.11 | 897 |
| 88 | CONH | H | COOH | peracetylglucosyl | 62.93/62.91, 7.64/7.27, 6.25/6.38 | 897 |
| 89 | CONH | H | COOH | galactosyl | 64.26/64.10, 8.30/8.14, 7.69/7.74 | 729 |
| 90 | CONH | H | COOH | glucosyl | 64.26/64.33, 8.30/8.17, 7.69/7.47 | 729 |
| 91 | C(O)O | Ac | $CH_2OAc$ | H | 69.67/69.71, 8.69/8.68, 6.59/6.54 | 638 |
| 92 | C(O)O | Ac | $CH_2OAc$ | $CH_3$ | 70.01/70.03, 8.81/8.84, 6.45/6.39 | 652 |
| 93 | C(O)O | Ac | $CH_2OAc$ | Pyridin-3-yl | 70.56/70.45, 8.18/8.23, 7.84/8.00 | 715 |
| 94 | C(O)O | Ac | $CH_2OAc$ | peracetylgalactosyl | 63.27/63.27, 7.60/7.51, 4.34/4.37 | 968 |
| 95 | C(O)O | Ac | $CH_2OAc$ | peracetylglucosyl | 63.27/63.29, 7.60/7.64, 4.34/4.30 | 968 |
| 96 | C(O)O | Ac | $CH_2OAc$ | galactosyl | 64.56/64.48, 8.19/8.17, 5.25/5.20 | 800 |
| 97 | C(O)O | Ac | $CH_2OAc$ | glucosyl | 64.56/64.50, 8.19/8.24, 5.25/5.23 | 800 |
| 98 | C(O)O | H | $CH_2OH$ | H | 71.57/71.59, 9.28/9.30, 7.59/7.54 | 554 |
| 99 | C(O)O | H | $CH_2OH$ | $CH_3$ | 71.92/72.01, 9.41/9.42, 7.40/7.47 | 568 |
| 100 | C(O)O | H | $CH_2OH$ | Pyridin-3-yl | 72.35/72.31, 8.63/8.57, 8.88/8.97 | 631 |
| 101 | C(O)O | H | $CH_2OH$ | peracetylgalactosyl | 63.85/63.79, 7.87/7.75, 4.75/4.70 | 884 |
| 102 | C(O)O | H | $CH_2OH$ | peracetylglucosyl | 63.85/63.77, 7.87/7.89, 4.75/4.81 | 884 |
| 103 | C(O)O | H | $CH_2OH$ | galactosyl | 65.43/65.47, 8.59/8.47, 5.87/5.77 | 716 |
| 104 | C(O)O | H | $CH_2OH$ | glucosyl | 65.43/65.40, 8.59/8.54, 5.87/5.91 | 716 |
| 105 | C(O)O | Ac | COOH | H | 68.94/68.91, 8.43/8.55, 6.89/6.78 | 610 |
| 106 | C(O)O | Ac | COOH | $CH_3$ | 69.31/69.30, 8.56/8.61, 6.74/6.69 | 624 |
| 107 | C(O)O | Ac | COOH | Pyridin-3-yl | 69.94/71.38, 7.92/7.88, 8.16/8.27 | 687 |
| 108 | C(O)O | Ac | COOH | peracetylgalactosyl | 62.60/62.51, 7.40/7.52, 4.47/4.54 | 940 |
| 109 | C(O)O | Ac | COOH | peracetylglucosyl | 62.60/62.47, 7.40/7.41, 4.47/4.60 | 940 |
| 110 | C(O)O | Ac | COOH | galactosyl | 63.79/63.87, 7.97/7.84, 5.44/5.34 | 772 |
| 111 | C(O)O | Ac | COOH | glucosyl | 63.79/63.87, 7.97/7.84, 5.44/5.34 | 772 |
| 112 | C(O)O | H | COOH | H | 71.70/71.54, 9.48/9.57, 10.14/10.03 | 553 |
| 113 | C(O)O | H | COOH | $CH_3$ | 70.19/70.24, 8.84/8.78, 7.22/7.31 | 582 |
| 114 | C(O)O | H | COOH | Pyridin-3-yl | 70.78/70.69, 8.13/8.15, 8.69/8.58 | 645 |
| 115 | C(O)O | H | COOH | peracetylgalactosyl | 62.86/62.78, 7.52/7.49, 4.68/4.57 | 898 |
| 116 | C(O)O | H | COOH | peracetylglucosyl | 62.86/62.80, 7.52/7.51, 4.68/4.59 | 898 |
| 117 | C(O)O | H | COOH | galactosyl | 64.18/64.23, 8.15/8.07, 5.76/5.68 | 730 |
| 118 | C(O)O | H | COOH | glucosyl | 64.18/64.09, 8.15/8.21, 5.76/5.90 | 730 |

TABLE 2

Prepared terpenes of the general formula I, where
------ is double bond and $R^3$ is H (Ac = acetyl)

| | Substituents | | | Heteroatoms | | | | CHN analysis | MS analysis |
|---|---|---|---|---|---|---|---|---|---|
| | X | $R^1$ | $R^2$ | A | B | Y | m | [% C, % H, % N] [calc./found] | $[M + H]^+$ |
| 119 | C(O)O | Ac | $CH_2OAc$ | NH | CH | CH | 1 | 73.67/73.55, 9.04/9.14, 2.20/2.09 | 636 |
| 120 | C(O)O | Ac | $CH_2OAc$ | CH | N | CH | 1 | 73.67/73.68, 9.04/9.09, 2.20/2.22 | 636 |
| 121 | C(O)O | Ac | $CH_2OAc$ | CH | S | CH | 1 | 71.74/71.65, 8.65/8.58 | 653 |
| 122 | C(O)O | Ac | $CH_2OAc$ | N | S | CH | 1 | 69.80/69.75, 8.48/8.54, 2.14/2.04 | 654 |
| 123 | C(O)O | Ac | $CH_2OAc$ | N | CH | S | 1 | 69.80/69.81, 8.48/8.59, 2.14/2.25 | 654 |
| 124 | C(O)O | Ac | $CH_2OAc$ | N | NH | CH | 1 | 71.67/71.50, 8.86/8.74, 4.40/4.51 | 637 |
| 125 | C(O)O | Ac | $CH_2OAc$ | N | O | CH | 1 | 71.55/71.48, 8.69/8.74, 2.20/2.04 | 638 |
| 126 | C(O)O | Ac | $CH_2OAc$ | N | CH | N | 2 | 72.19/72.27, 8.70/8.59, 4.32/4.28 | 649 |
| 127 | C(O)O | Ac | $CH_2OAc$ | CH | CH | CH | 2 | 76.12/76.14, 9.04/9.12, | 647 |
| 128 | C(O)O | Ac | $CH_2OAc$ | N | CH | CH | 2 | 74.15/74.06, 8.87/8.92, 2.16/2.24 | 648 |
| 129 | C(O)O | Ac | $CH_2OAc$ | CH | N | CH | 2 | 74.15/74.12, 8.87/8.96, 2.16/2.08 | 648 |
| 130 | C(O)O | Ac | $CH_2OAc$ | CH | CH | N | 2 | 74.15/74.15, 8.87/8.65, 2.16/2.04 | 648 |
| 131 | C(O)O | H | $CH_2OH$ | N | CH | NH | 1 | 73.87/73.69, 9.48/9.56, 5.07/5.14 | 553 |
| 132 | C(O)O | H | $CH_2OH$ | CH | NH | CH | 1 | 76.18/76.20, 9.68/9.59, 2.54/2.65 | 552 |
| 133 | C(O)O | H | $CH_2OH$ | CH | S | CH | 1 | 73.90/73.78, 9.21/9.14 | 569 |
| 134 | C(O)O | H | $CH_2OH$ | N | CH | S | 1 | 71.66/71.54, 9.02/8.88, 2.46/2.27 | 570 |
| 135 | C(O)O | H | $CH_2OH$ | N | CH | N | 2 | 74.43/74.39, 9.28/9.01, 4.96/5.07 | 565 |
| 136 | C(O)O | H | $CH_2OH$ | N | CH | CH | 2 | 76.69/76.54, 9.48/9.34, 2.48/2.51 | 564 |
| 137 | C(O)O | H | $CH_2OH$ | CH | N | CH | 2 | 76.69/76.60, 9.48/9.52, 2.48/2.30 | 564 |
| 138 | C(O)O | Ac | COOH | CH | NH | CH | 1 | 73.11/72.98, 8.79/8.65, 2.30/2.25. | 608 |

TABLE 2-continued

| Prepared terpenes of the general formula I, where ------ is double bond and $R^3$ is H (Ac = acetyl) | | | | | | | | | |
|---|---|---|---|---|---|---|---|---|---|
| | Substituents | | | Heteroatoms | | | | CHN analysis | MS analysis |
| | X | $R^1$ | $R^2$ | A | B | Y | m | [% C, % H, % N] [calc./found] | $[M + H]^+$ |
| 139 | C(O)O | Ac | COOH | CH | S | CH | 1 | 71.12/71.21, 8.39/0.14 | 625 |
| 140 | C(O)O | Ac | COOH | N | S | CH | 1 | 69.09/68.98, 8.21/8.07, 2.24/2.05 | 626 |
| 141 | C(O)O | Ac | COOH | N | CH | S | 1 | 69.09/69.00, 8.21/8.27, 2.24/2.14 | 626 |
| 142 | C(O)O | Ac | COOH | N | CH | N | 2 | 71.58/71.49, 8.44/8.24, 4.51/4.29 | 621 |
| 143 | C(O)O | Ac | COOH | N | CH | CH | 2 | 73.63/73.59, 8.62/8.76, 2.26/2.07 | 620 |
| 144 | C(O)O | Ac | COOH | CH | N | CH | 2 | 73.63/73.63, 8.62/8.54, 2.26/2.30 | 620 |
| 145 | C(O)O | H | COOH | CH | NH | CH | 1 | 74.30/74.05, 9.09/8.94, 2.48/2.39 | 566 |
| 146 | C(O)O | H | COOH | CH | S | CH | 1 | 72.13/72.01, 8.65/8.54 | 583 |
| 147 | C(O)O | H | COOH | N | S | CH | 1 | 69.95/70.09, 8.46/8.67, 2.40/2.39 | 584 |
| 148 | C(O)O | H | COOH | N | CH | S | 1 | 69.95/70.11, 8.46/8.38, 2.40/2.51 | 584 |
| 149 | C(O)O | H | COOH | N | CH | N | 2 | 72.63/72.56, 8.71/8.65, 4.84/4.94 | 579 |
| 150 | C(O)O | H | COOH | N | CH | CH | 2 | 74.83/74.68, 8.90/8.70, 2.42/2.38 | 578 |
| 151 | C(O)O | H | COOH | CH | N | CH | 2 | 74.83/74.80, 8.90/8.94, 2.42/2.47 | 578 |
| 152 | CONH | Ac | $CH_2OAc$ | CH | NH | CH | 1 | 73.78/73.69, 9.21/9.41, 4.41/4.29 | 635 |
| 153 | CONH | Ac | $CH_2OAc$ | CH | S | CH | 1 | 71.85/71.93, 8.81/8.68, 2.15/2.21 | 652 |
| 154 | CONH | Ac | $CH_2OAc$ | N | S | CH | 1 | 69.90/69.87, 8.65/8.67, 4.29/4.14 | 653 |
| 155 | CONH | Ac | $CH_2OAc$ | N | CH | S | 1 | 69.90/69.99, 8.65/8.48, 4.29/4.33 | 653 |
| 156 | CONH | Ac | $CH_2OAc$ | N | CH | N | 2 | 72.30/72.18, 8.87/8.76, 6.49/6.31 | 648 |
| 157 | CONH | Ac | $CH_2OAc$ | N | CH | CH | 2 | 74.27/74.18, 9.04/8.97, 4.33/4.51 | 647 |
| 158 | CONH | Ac | $CH_2OAc$ | CH | N | CH | 2 | 74.27/74.32, 9.04/9.13, 4.33/4.41 | 647 |
| 159 | $CH_2O$ | Ac | $CH_2OAc$ | CH | S | CH | 1 | 73.31/73.28, 9.15/9.21 | 638 |
| 160 | $CH_2O$ | Ac | $CH_2OAc$ | CH | N | CH | 2 | 75.79/75.68, 9.38/9.38, 2.21/2.24 | 634 |
| 161 | $CH_2NH$ | H | $CH_2OH$ | CH | S | CH | 1 | 75.90/75.92, 10.01/10.13, 2.53/2.48 | 554 |
| 162 | $CH_2NH$ | H | $CH_2OH$ | CH | N | CH | 2 | 78.78/78.91, 10.28/10.26, 5.10/5.03 | 549 |
| 163 | $CH_2O$ | H | COOH | CH | N | CH | 2 | 76.69/76.67, 9.48/9.52, 2.48/2.50 | 564 |
| 164 | $CH_2O$ | H | COOH | CH | S | CH | 1 | 73.90/73.93, 9.21/9.28 | 569 |

Example 7

Cytotoxicity of New Compounds for Neuronal Cells

The SH-SY5Y human neuroblastoma cell line obtained from ECACC (The European Collection of Authenticated Cell Cultures) was cultivated in Dulbecco's modified Eagle's Medium and Ham's F12 Nutrient Mixture (DMEM: F-12, 1:1), supplemented with 10% fetal bovine serum (FBS) and 1% penicillin and streptomycin at 37° C. in a humidified atmosphere 5% $CO_2$, 95% humidity in passage limit up to ECACC+20. The assay was performed in 96-well microplate with 7000 SH-SY5Y cells per well. After 48 h, old DMEM/F12 media was removed by fresh media containing tested compounds at 0.1, 1 and 10 μM concentrations for 24 h. Glial cell line A-172 purchased from ATCC and grown in same conditions as SH-SY5Y cell line. A-172 cells were seeded in density 2000 cells per well and growing medium was replaced by treatment medium containing tested compounds in 0.1, 1 and 10 μM concentration; or in higher concentrations for R-LA or NAC positive controls for 48 hours. All tested compounds dissolved in DMSO were added into the medium. The maximum concentration of DMSO in media was kept below 0.1% (v/v). The cell viability was measured by Calcein AM (1 mg/ml ThermoFisher) viability assay. Solution of Calcein AM in PBS (0.75 μM) was pipetted to cells and incubated for 50 min. After that the fluorescence was measured at 488/517 nm (excitation/emission) using microplate reader Infinite M200 (TECAN). Calcein AM assay is based on the dye-intracellular-esterase cleavage of non-fluorescent dye (Calcein AM) by living cells to fluorescent dye (Calcein), while dying cells lose such ability. The values in Table 2 show the % of viability compared to control for all tested compounds. The results from DMSO control (medium with DMSO, <0.1% (v/v)) was postulated as 100% viability (see the first line of Table 2). As shown in Table 2, all derivatives were proved to not induce a decrease in viability in neuron-like cells while in astrocytes compounds 3 and 4 together with 1000 μM NAC showed a slight decrease in percentage of living cells.

TABLE 2

Cytotoxicity of studied pentacyclic triterpenes and positive controls N-acetyl cysteine (NAC) and R-LA on neuron-like SH-SY5Y and glial A172 cells. The data are expressed as percentages of DMSO control; the mean ± SEM from two independent experiments.

| compound | neuron-like SH-SY5Y cells | | | | | | glial A-172 cells | | | | | |
|---|---|---|---|---|---|---|---|---|---|---|---|---|
| | 0.1 μM | ±SEM | 1 μM | ±SEM | 10 μM | ±SEM | 0.1 μM | ±SEM | 1 μM | ±SEM | 10 μM | ±SEM |
| 3 | 115.8 | 2.78 | 145.0 | 3.10 | 137.4 | 1.82 | 95.5 | 3.74 | 98.2 | 2.43 | 71.7 | 1.07 |
| 4 | 99.9 | 3.52 | 146.1 | 3.28 | 142.5 | 2.89 | 104.2 | 2.80 | 97.9 | 2.62 | 83.6 | 4.86 |
| 5 | 91.9 | 4.05 | 106.4 | 3.84 | 129.5 | 3.32 | 96.6 | 3.56 | 100.0 | 2.41 | 90.8 | 2.40 |
| 6 | 92.1 | 4.39 | 96.2 | 5.01 | 113.5 | 1.69 | 99.9 | 1.09 | 98.4 | 3.11 | 96.2 | 4.64 |

TABLE 2-continued

Cytotoxicity of studied pentacyclic triterpenes and positive controls N-acetyl cysteine (NAC) and R-LA on neuron-like SH-SY5Y and glial A172 cells. The data are expressed as percentages of DMSO control; the mean ± SEM from two independent experiments.

| compound | neuron-like SH-SY5Y cells | | | | | | glial A-172 cells | | | | | |
|---|---|---|---|---|---|---|---|---|---|---|---|---|
| NAC | 10 μM | ±SEM | 100 μM | ±SEM | 1000 μM | ±SEM | 10 μM | ±SEM | 100 μM | ±SEM | 1000 μM | ±SEM |
| | 92.7 | 3.68 | 97.5 | 3.70 | 101.5 | 5.25 | 102.9 | 2.65 | 96.6 | 5.86 | 83.0 | 3.69 |
| R- Lipoic acid | | | | | | | 0.5 μM | ±SEM | 5 μM | ±SEM | 50 μM | ±SEM |
| | | | | | | | 107.1 | 3.21 | 100.9 | 3.06 | 95.2 | 2.25 |

[a]viabilities are expressed as means ± SEM, compounds were tested in triplicates in at least two independent experiments.

Example 8

Viability Tests on Human Neuroblastoma Cell Line SH-SY5Y (Differentiated Phenotype)

Similarly, as in previous "Safety test", the SH-SY5Y cells were seeded at density 7000 cells/well. After 48 h differentiation, old 1% DMEM/F12 media was replaced by fresh media containing 800 μM salsolinol (SAL) and tested compounds in 0.1, 1 and 10 μM concentrations. N-acetylcystein were chosen as positive control. After 24 hours, the cell viability was measured by Calcein AM viability assay. The values in Table 2 show % of viability of all tested compounds relative to control. The control (medium with DMSO, <0.1% (v/v)) was postulated as 100% viability (see the first line of the table), while the SAL exposure lead to decrease of viability to 65.4±0.97%. NAC (1000 μM, 81.54±1.59%) demonstrated potent protective effects which were in close correlation with the published literature data (Wanpen et al., Brain Res. 2004, 1005, 67). As shown in Table 2, derivatives 3-5 demonstrated strong stimulatory effect on neuronal SH-SY5Y cells. Overall, triterpene derivatives 3, 4 and 5 demonstrated better effect than 1000 μM NAC and had higher efficiency in the term of active concentrations.

TABLE 3

The effect of new pentacyclic triterpenes and positive control N-acetyl cysteine (NAC) on viability of human neuroblastoma cell line SH-SY5Y in salsolinol-induced model of PD.

| | Neuroprotective effect (% of control) | | | |
|---|---|---|---|---|
| Compound | 10 μM | 100 μM | 1000 μM | p value |
| NAC | N/A | N/A | 16.15 | >0.001 |
| | 0.1 μM | 1 μM | 10 μM | |
| 3 | N/A | 33.10 | 21.50 | >0.001 |
| 4 | N/A | 33.70 | 33.99 | >0.001 |
| 5 | N/A | N/A | 18.96 | >0.001 |
| 6 | N/A | N/A | 7.38 | n.s. |

N/A = no protection; The data are expressed as differences between 800 μM SAL and co-treatment groups (compounds) means, with significances after statistical analysis (ANOVA, Tukey post hoc test).

Example 9

The Effect of New Pentacyclic Triterpenes and Positive Control N-acetyl Cysteine (NAC) on Caspase-3,7 Activity in Salsolinol-Induced Model of PD on Human Neuroblastoma Cell Line SH-SY5Y Similarly, as shown in previous assay, cells grew on 96 multiwell plates at density 20000 cells per well underwent differentiation and treatment procedure for salsolinol model. After 24 hour co-treatment with salsolinol, caspase-3,7 (casp-3,7) activity as marker of apoptosis was quantified by its substrate Ac-DEVD-AMC according to Carrasco et al. (2003, *BioTechniques,* 34, 1064-1067). In this model, overall casp-3,7 activity induced by 800 μM SAL was consider as 100% and thus the reduction in casp-3,7 was observed after treatment with the protective terpenoid derivatives. As shown in Table 4 and FIG. 2, 800 μM SAL induced 2.9-fold increase. More importantly new compounds at 10 μM demonstrated comparable (compound 3) or better (4) reduction of caspase-3,7 activity than NAC. Other derivatives like 5 and 6 showed also positive effect on casp-3,7 activity. Taken together, all examples showed reducing effect on casp-3,7 activity. Especially derivatives 3, 4 and 5 showed better efficacy than NAC positive control due to their lower used concentration (10-fold more effective than positive controls).

TABLE 4

The effect of new pentacyclic triterpenes and positive controls N-acetyl cysteine (NAC) on caspase-3,7 activity induced by Salsolinol (SAL). The data are expressed as percentages of control (800 μM SAL) as the mean ± SEM of at least two independent experiments.

Caspase-3,7 activity (% of reduction)

| | average | ±SEM |
|---|---|---|
| DMSO Control | 34.19 | 2.49 |
| SAL (800 μM) | 100.00 | 3.14 |

| Compound | 1 μM | ±SEM | 10 μM | ±SEM |
|---|---|---|---|---|
| 3 | 73.7 | 3.88 | 55.6 | 2.16 |
| 4 | 67.2 | 2.87 | 46.0 | 2.67 |
| 5 | 86.8 | 8.52 | 76.5 | 6.12 |
| 6 | 93.2 | 5.74 | 88.3 | 5.58 |
| NAC | 100 μM | ±SEM | 1000 μM | ±SEM |
| | 60.4 | 1.08 | 55.2 | 3.19 |

Example 10

The Effect of New Pentacyclic Triterpenes and Positive Control N-Acetyl Cysteine (NAC) in 3-Nitropropionic Acid (3NPA)-Induced Model of Huntington'S Disease on Human Neuron-Like SH-SY5Y Cells and Glial A-172 Cells Before application of toxin 3-nitropropionic acid (3NPA) for mimicking Huntington's disease, the 3NPA was dissolved in water and neutralized by sodium hydroxide. SH-SY5Y cells were seeded in the same density and differentiated by the procedure shown above. Astrocyte cells A-172 were also seeded as described in previous section. Both cell lines were co-treated by 3NPA (20 mM for SH-SY5Y cells, mM for A-172 cells) and tested compounds at 0.1, 1 and 10 μM concentration for 48 h. NAC (SH-SY5Y cell line) and R-lipoic acid (R-LA) were used as positive controls. As shown in Table 5, all derivatives showed neuroprotective effect on SH-SY5Y cells slightly lower than 100 μM NAC, however at much lower concentrations. Contrary to NAC, compounds 3 and 5 showed a positive effect comparable to R-LA control, a known protective agent for astrocytes (Molinari et al., Oxid. Med. Cell. Longev. 2019, 2019, 2843121). Taken together, triterpene derivatives demonstrated higher efficacy in PD and HD treatment (salsolinol model) than positive control NAC due to the protective activity on both neuronal and astrocyte cell lines at lower micromolar concentrations.

TABLE 5

The protective effect of new pentacyclic triterpenes and positive controls N-acetyl cysteine (NAC) and R-lipoic acid (R-LA) in in vitro models of Huntington's disease on human neuron-like SH-SY5Y cells and astrocyte A-172 cells.
N/A = no protection; The data are expressed as differences between 20 mM 3NPA (SH-SY5Y) and 10 mM 3NPA (A-172) and co-treatment groups (compounds) means. of three (SH-SY5Y) or at least four (A-172) independent experiments in triplicates.

| | neuron-like SH-SY5Y cells Neuro-protective effec t (% of control) | | | Astrocyte A-172 cells Astro-protective effect (% of control) | | |
|---|---|---|---|---|---|---|
| Compound | 10 μM | 100 μM | 1000 μM | 0.5 μM | 5 μM | 50 μM |
| NAC | N/A | 51.35 | 65.72 | N/A | N/A | N/A |
| R-LA | | | | N/A | 13.27 | 14.87 |
| | 0.1 μM | 1 μM | 10 μM | 0.1 μM | 1 μM | 10 μM |
| 3 | N/A | 39.96 | 24.13 | N/A | 11.98 | N/A |
| 4 | N/A | 32.36 | 28.98 | 7.38 | 3.25 | N/A |
| 5 | N/A | N/A | 20.63 | N/A | 12.87 | 14.05 |
| 6 | N/A | N/A | 20.53 | 4.27 | 4.57 | 7.45 |

Example 11

Measurement of Oxidative Stress (OS) on Human Neuroblastoma Cell Line SH-SY5Y-3NPA-Induced Model of Huntington'S Disease Similarly, to previous assay, cells grown on 96-multiwell plates at density 20000 cells per well underwent differentiation and treatment procedure with 3-nitropropionic acid (3NPA) in this model. After 24 hours of co-treatment with 20 mM 3NPA, superoxide radical's formation as a marker of oxidative stress was quantified by dihydroethidium according to Kim et al. (2017, J. Med. Food, 20, 140-151). Briefly, neuron-like SH-SY5Y cells were centrifuged at 500 g for 5 min and 30 s, then media were replaced by 10 μM DHE PBS solution and kept at room temperature for 30 min. After that, DHE was read at 500 nm/580 nm (excitation/emission) by Infinite M200 Pro (Tecan) microplate reader. DHE is cell permeable dye which is selective for superoxide radical detection. Overall oxidative stress achieved by 20 mM 3NPA was consider as 100% and thus the reduction in superoxide radical's formation (OS reducing effect) was determined. As shown in Table 6 and FIG. 2, 20 mM 3NPA induced 2.7-fold increase in superoxide radical's formation. At 10 μM, all new terpenoid derivatives demonstrated comparable OS reducing effect as 100 μM NAC, except compound 3 which showed even stronger activity toward oxidative stress. Taken together, all test compounds showed higher potency than the positive control at the concentrations responsible for OS-reducing activity (all compounds were 10-fold more effective than positive controls).

TABLE 6

The oxidative stress (OS)-reducing effect of new pentacyclic triterpenes and positive controls N-acetyl cysteine (NAC) in in vitro model of Huntington's disease on human neuron-like SH-SY5Y cells after 24 hours. Superoxide radical formation (oxidative stress) %

| | average | | ±SEM | | | |
|---|---|---|---|---|---|---|
| DMSO CTR | 37.08 | | 1.14 | | | |
| 3-NPA 20 mM | 100 | | 2.50 | | | |
| Compound | 0.1 μM | ±SEM | 1 μM | ±SEM | 10 μM | ±SEM |
| 3 | 88.4 | 4.92 | 79.0 | 3.48 | 81.9 | 2.11 |
| 4 | 84.7 | 6.37 | 78.5 | 4.46 | 65.8 | 5.63 |
| 5 | 94.1 | 3.93 | 87.3 | 3.86 | 87.1 | 3.54 |
| 6 | 92.2 | 6.37 | 89.9 | 4.46 | 88.0 | 5.63 |
| NAC | 10 μM | ±SEM | 100 μM | ±SEM | 1000 μM | ±SEM |
| | 79.6 | 5.99 | 79.7 | 8.18 | 48.5 | 2.84 |

Example 12

Formulations

The growth regulatory formulations usually contain from 0.1 to 99% by weight, especially from 0.1 to 95% by weight, of active ingredient mixture comprising a new terpenoid derivative of this invention, from 1 to 99.9% by weight of a solid or liquid formulation adjuvant, and from 0 to 25% by weight, especially from 0.1 to 25% by weight, of a surfactant. Whereas commercial products are usually formulated as concentrates, the end user will normally employ dilute formulations. The compositions may also comprise further ingredients, such as stabilizers, e.g., vegetable oils or epoxidized vegetable oils (epoxidized coconut, rapeseed oil or soybean oil), antifoams, e.g., silicone oil, preservatives, viscosity regulators, binders, tackifiers, and also fertilisers or other active ingredients. Preferred formulations have especially the following compositions: (%=percent by weight):

F1. Wettable Powders

| | a) | b) | c) | d) |
|---|---|---|---|---|
| active ingredient mixture | 5% | 25% | 50% | 80% |
| sodium lignosulfonate | 4% | — | 3% | — |
| sodium lauryl sulphate | 2% | 3% | — | 4% |
| sodium diisobutylnaphthalene-sulfonate | — | 6% | 5% | 6% |
| octylphenol polyglycol ether (7-8 mol ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

F2. Suspension Concentrates

| | a) | b) | c) | d) |
|---|---|---|---|---|
| active ingredient mixture | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjutants, giving a suspension concentrate from which suspensions of any desired concentration can be obtained by dilution with water.

F3. Dry Capsules 5000 capsules, each of which contain 0.25 g of one of the new terpenoid derivative as active ingredient, are prepared as follows:

Composition: Active ingredient: 1250 g; Talc: 180 g; Wheat starch: 120 g; Magnesium stearate: 80 g; Lactose 20 g.

Preparation process: The powdered substances mentioned are pressed through a sieve of mesh width 0.6 mm Portions of 0.33 g of the mixture are transferred to gelatine capsules with the aid of a capsule-filling machine.

F4. Soft Capsules 5000 soft gelatine capsules, each of which contain 0.05 g of one of the new terpenoid derivative as active ingredient, are prepared as follows:

Composition: 250 g Active ingredient+2 litres Lauroglycol

Preparation process: The powdered active ingredient is suspended in Lauroglykol® (propylene glycol laurate, Gattefosse S.A., Saint Priest, France) and ground in a wet-pulveriser to a particle size of about 1 to 3 mm Portions of in each case 0.419 g of the mixture are then transferred to soft gelatine capsules by means of a capsule-filling machine.

F5. Soft Capsules 5000 soft gelatine capsules, each of which contain 0.05 g of one of the new terpenoid derivative as active ingredient, are prepared as follows:

Composition: 250 g Active ingredient+1 litre PEG 400+1 litre Tween 80

Preparation process: The powdered active ingredient is suspended in PEG 400 (polyethylene glycol of Mr between 380 and about 420, Sigma, Fluka, Aldrich, USA) and Tween® 80 (polyoxyethylene sorbitan monolaurate, Atlas Chem. Inc., Inc., USA, supplied by Sigma, Fluka, Aldrich, USA) and ground in a wet-pulveriser to a particle size of about 1 to 3 mm Portions of in each case 0.43 g of the mixture are then transferred to soft gelatine capsules by means of a capsule-filling machine.

Example 13

Formulation of Tablets with Controlled Release

One tablet contains, for example, 300-350 mg of terpenoid derivative as active ingredient. Excipient with known effect: Each tablet contains 150 to 200 mg of a retardant (Methocel, Parteck® SRP 80, Kollidon® SR, Kollidon 25, chitosan, alginate), as well as a lubricant (magnesium stearate), active substances (VH), binders (Prosolv SMCC 90).

The dosage form is a controlled release tablet.

Tablet preparation: Tablets are prepared by direct compression. First, the calculated amount of retarding component (Methocel, Parteck® SRP 80, Kollidon® SR, Kollidon 25, chitosan, alginate), weighing agent (magnesium stearate), active ingredient (VH), binder (Prosolv SMCC 90) are weighed. The resulting mixture is then homogenized in a homogenizer (Retsch MM200-Retsch GmbH, Haan). It is recommended to carry out the homogenization at three frequencies: 10 oscillations/s, 13 and 15 oscillations/s for 1 minute each. The tablet is then transferred to a hand press. The tablets are compressed at a load of 8 kN for 5 minutes. The load is selected with respect to the desired tablet strength of 0.8 to MPa. The tablet weight is 500±5 mg.

Hydrophilic Matrix Tablets with Hypromellose

The tablets are prepared by the direct compression method as described above.

The tablet weight was 500±5 mg. Composition of hydrophilic tablets with hypromellose in wt. %:

| Formulation | A1 | A2 | A3 |
|---|---|---|---|
| Prosolv SMCC 90 | 49% | 49% | 49% |
| Methocel K4M | — | 30% | — |
| Methocel K15M | 30% | — | — |
| Methocel K100M | — | — | 30% |
| Active substance | 20% | 20% | 20% |
| Magnesium stearate | 1% | 1% | 1% |

Hydrophilic Matrix Tablets with Retarding Component Kollidon 25, Kollidon® SR, Parteck® SRP 80

The tablets are prepared by the direct compression method as described above.

The tablet weight was 500±5 mg. Composition of hydrophilic tablets in wt. %:

| Formulation | F1 | F2 | F3 | F4 | F5 |
|---|---|---|---|---|---|
| Prosolv ® SMCC 90 | 49% | 49% | 49% | 49% | 49% |
| Kollidon 25 | 30% | 20% | 10% | — | — |
| Kollidon ® SR | — | — | — | 30% | — |
| Parteck ® SRP 80 | — | — | — | — | 30% |

-continued

| Formulation | F1 | F2 | F3 | F4 | F5 |
|---|---|---|---|---|---|
| Active substance | 20% | 30% | 40% | 20% | 20% |
| Magnesium stearate | 1% | 1% | 1% | 1% | 1% |

Hydrophilic Matrix Tablets Containing LubriTose™ MCC, Methocel K15M nebo Methocel K4M The tablets are prepared by the direct compression method as described above.

The tablet weight was 500±5 mg. Composition of hydrophilic tablets in wt. %:

| Formulation | A1 | A2 |
|---|---|---|
| LubriTose ™ MCC | 50% | 50% |
| Methocel K15M | 30% | — |
| Methocel K4M | — | 30% |
| Active substance | 20% | 20% |

The invention claimed is:

1. A method of treatment of neurodegenerative disease, comprising the step of administering at least one terpenoid derivative of the general formula I,

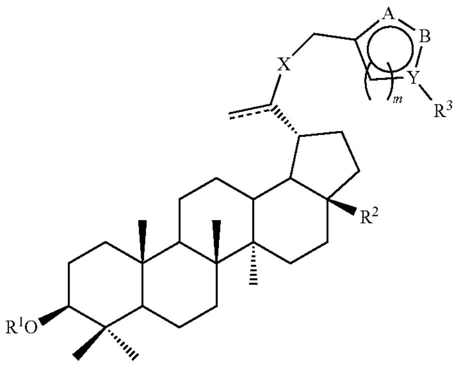

I wherein,

------ is single or double bond;

X is independently selected from $CH_2NH$, $CH_2O$, C(O)NH, C(O)O

A, B, and Y are independently on each occurrence selected from the group consisting of CH, C, N, NH, O, S;

m=1, 2, 3;

$R^1$ is independently selected from H—, $CH_3(CH_2)_nCO$— or $HOOC(CH_2)_nCO$— and n=0-5;

$R^2$ is independently selected from —$CH_2OH$, —$CH_2O(CH_2)_nCH_3$, —$CH_2OC(O)(CH_2)_nCH_3$, —COOH, —$COO(CH_2)_nCH_3$ and $COO(CH_2)Ph$, wherein n=0-5;

$R^3$ is independently selected on each occurrence from C6-C12 aryl, heteroaryl containing 5-8 atoms in the aromatic ring of that at least one is heteroatom selected from N, O, S; glucose, galactose, mannose, rhamnose, lactose, ribose, arabinose, 2-deoxyglucose, 2-deoxygalactose, 2-deoxymannose, and their peracetylated derivatives; while $R^3$ is not present when Y is O or S;

or their pharmaceutically acceptable salts to a subject in need of such treatment.

2. The method according to claim 1 wherein $R^3$ is selected from the group consisting of phenyl, triazolyl, pyridinyl, thiophenyl, imidazolyl, furyl, and pyrazinyl.

3. The method according to claim 1 wherein $R^3$ is selected from the group consisting of sugars, consisting of glucose, galactose, mannose, rhamnose, lactose, ribose, arabinose, 2-deoxyglucose, 2-deoxygalactose, 2-deoxymannose and their peracetylated derivatives.

4. The method according to claim 1, wherein the neurodegenerative disease is selected from amyotrophic lateral sclerosis, Parkinson's disease, Alzheimer's disease, Huntington's disease, progressive supranuclear palsy, corticobasal degeneration, frontotemporal dementia, Lewy body dementia, multiple system atrophy, chronic traumatic encephalopathy, and spinocerebellar ataxia.

5. A method of treatment of neurodegenerative disease, comprising the step of administering at least one terpenoid derivative of the general formula Ia, Ia

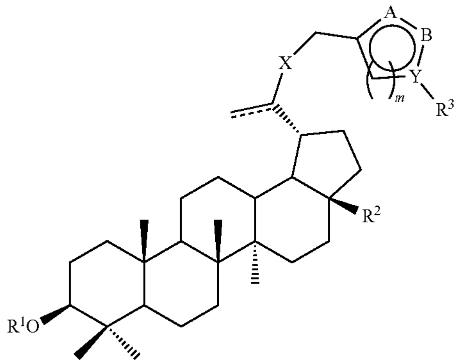

wherein,

------ is single or double bond;

X is independently selected from —$CH_2O$—, —C(O)NH—, —C(O)O—

A, B, and Y are independently on each occurrence selected from the group consisting of CH, C, N, NH, O, S;

m=1, 2, 3;

$R^1$ is independently selected from H—, $CH_3(CH_2)_nCO$— or $HOOC(CH_2)_nCO$— and n=0-5;

$R^2$ is independently selected from —$CH_2OH$, —$CH_2O(CH_2)_nCH_3$, —$CH_2OC(O)(CH_2)_nCH_3$, —COOH, —$COO(CH_2)_nCH_3$ and $COO(CH_2)Ph$, wherein n=0-5;

$R^3$ is independently selected on each occurrence from C6-C12 aryl; heteroaryl containing 5-8 atoms in the aromatic ring of that at least one is heteroatom selected from N, O, S; glucose, galactose, mannose, rhamnose, lactose, ribose, arabinose, 2-deoxyglucose, 2-deoxygalactose, 2-deoxymannose, and their peracetylated derivatives; while $R^3$ is not present when Y is O or S;

provided that if X is C(O)NH or C(O)O, $R^1$ is $CH_3CO$—, $R^2$ is —$CH_2OC(O)CH_3$ or COOH, A=B=C=N and m=1; then $R^3$ is not phenyl, 4-aminophenyl, 4-thiocyanatophenyl, 2-carboxyphenyl, peracetylglucosyl, peracetylgalactosyl;

or

X is —$CH_2NH$—,

A, B, and Y are independently on each occurrence selected from the group consisting of CH, C, N, NH, O, S;

m=1, 2, 3;

$R^1$ is independently selected from H—, $CH_3(CH_2)_nCO$— or $HOOC(CH_2)_nCO$— and n=0-5;

$R^2$ is independently selected from —$CH_2OH$, —$CH_2O(CH_2)_nCH_3$, —$CH_2OC(O)(CH_2)_nCH_3$, —COOH, —$COO(CH_2)_nCH_3$ and $COO(CH_2)Ph$, wherein n=0-5;

$R^3$ is independently selected on each occurrence from heteroaryl containing 5-8 atoms in the aromatic ring of that at least one is heteroatom selected from N, O, S; glucose, galactose, mannose, rhamnose, lactose, ribose, arabinose, 2-deoxyglucose, 2-deoxygalactose, 2-deoxymannose, and their peracetylated derivatives; while $R^3$ is not present when Y is O or S;

or their pharmaceutically acceptable salts to a subject in need of such treatment.

6. The method according to claim 5, wherein the neurodegenerative disease is selected from amyotrophic lateral sclerosis, Parkinson's disease, Alzheimer's disease, Huntington's disease, progressive supranuclear palsy, corticobasal degeneration, frontotemporal dementia, Lewy body dementia, multiple system atrophy, chronic traumatic encephalopathy, and spinocerebellar ataxia.

7. A method of treatment of neurodegenerative disease, comprising the step of administering at least one terpenoid derivative to a subject in need of such treatment, wherein the at least one terpenoid derivative is selected from the group consisting of 30-1H-1,2,3-triazol-4-yl-methoxylup-20(29)-en-3,28-diol diacetate, 30-(1-methyl1H-1,2,3-triazol-4-yl)-methoxylup-20(29)-en-3,28-diol diacetate, 30-(1-phenyl1H-1,2,3-triazol-4-yl)-methoxylup-20(29)-en-3,28-diol diacetate, 30-(1-[pyridin-2-yl]-1H-1,2,3-triazol-4-yl)-methoxylup-20(29)-en-3,28-diol diacetate, 30-(1-[peracetyl glucos-1-yl]-1H-1,2,3-triazol-4-yl)-methoxylup-20(29)-en-3,28-diol diacetate, 30-(1-[peracetyl galactos-1-yl]-1H-1,2,3-triazol-4-yl)-methoxylup-20(29)-en-3,28-diol diacetate, 30-(1-[glucos-1-yl]-1H-1,2,3-triazol-4-yl)-methoxylup-20(29)-en-3,28-diol diacetate, 30-(1-[galactos-1-yl]-1H-1,2,3-triazol-4-yl)-methoxylup-20(29)-en-3,28-diol diacetate, 30-1H-1,2,3-triazol-4-yl-methoxylup-20(29)-en-3,28-diol, 30-(1-methyl1H-1,2,3-triazol-4-yl)-methoxylup-20(29)-en-3,28-diol, 30-(1-[peracetyl galactos-1-yl]-1H-1,2,3-triazol-4-yl)-methoxylup-20(29)-en-3,28-diol, 30-(1-[galactos-1-yl]-1H-1,2,3-triazol-4-yl)-methoxylup-20(29)-en-3,28-diol, 30-1H-1,2,3-triazol-4-yl-methylaminolup-20(29)-en-3,28-diol diacetate, 30-(1-methyl1H-1,2,3-triazol-4-yl)-methylaminolup-20(29)-en-3,28-diol diacetate, 30-(1-[peracetyl glucos-1-yl]-1H-1,2,3-triazol-4-yl)-methylaminolup-20(29)-en-3,28-diol diacetate, 30-(1-[peracetyl galactos-1-yl]-1H-1,2,3-triazol-4-yl)-methylaminolup-20(29)-en-3,28-diol diacetate, 30-(1-[glucos-1-yl]-1H-1,2,3-triazol-4-yl)-methylaminolup-20(29)-en-3,28-diol diacetate, 30-(1-[galactos-1-yl]-1H-1,2,3-triazol-4-yl)-methylaminolup-20(29)-en-3,28-diol diacetate, 30-1H-1,2,3-triazol-4-yl-methylaminolup-20(29)-en-3,28-diol, 30-(1-methyl1H-1,2,3-triazol-4-yl)-methylaminolup-20(29)-en-3,28-diol, 30-(1-[peracetyl glucos-1-yl]-1H-1,2,3-triazol-4-yl)-methylaminolup-20(29)-en-3,28-diol, 30-(1-[peracetyl galactos-1-yl]-1H-1,2,3-triazol-4-yl)-methylaminolup-20(29)-en-3,28-diol, 30-(1-[glucos-1-yl]-1H-1,2,3-triazol-4-yl)-methylaminolup-20(29)-en-3,28-diol, 30-(1-[galactos-1-yl]-1H-1,2,3-triazol-4-yl)-methylaminolup-20(29)-en-3,28-diol, 30-(1H-1,2,3-triazol-4-yl-methylamino)-3β-hydroxylup-20(29)-en-28-oic acid, 30-[(1-methyl1H-1,2,3-triazol-4-yl)-methylamino]-3β-hydroxylup-20(29)-en-28-oic acid, 30-{(1-[peracetyl glucos-1-yl]-1H-1,2,3-triazol-4-yl)-methylamino}-3β-hydroxylup-20(29)-en-28-oic acid, 30-{(1-[peracetyl galactos-1-yl]-1H-1,2,3-triazol-4-yl)-methylamino}-3β-hydroxylup-20(29)-en-28-oic acid, 30-{(1-[glucos-1-yl]-1H-1,2,3-triazol-4-yl)-methylamino}-3β-hydroxylup-20(29)-en-28-oic acid, 30-{(1-[galactos-1-yl]-

1H-1,2,3-triazol-4-yl)-methylamino}-3β-hydroxylup-20(29)-en-28-oic acid, 30-(1H-1,2,3-triazol-4-yl-methylamino)-3β-hydroxylup-20(29)-en-28-oic acid methyl ester, 30-(1H-1,2,3-triazol-4-yl-methoxy)-3β-hydroxylup-20(29)-en-28-oic acid, 30-{(1-[peracetyl galactos-1-yl]-1H-1,2,3-triazol-4-yl)-methoxy}-3β-hydroxylup-20(29)-en-28-oic acid, 30-{(1-[galactos-1-yl]-1H-1,2,3-triazol-4-yl)-methoxy}-3β-hydroxylup-20(29)-en-28-oic acid, 30-(1H-1,2,3-triazol-4-yl-methoxy)-3β-hydroxylup-20(29)-en-28-oic acid methyl ester, 30-{(1-[peracetyl glucos-1-yl]-1H-1,2,3-triazol-4-yl)-methoxy}-3β-hydroxylup-20(29)-en-28-oic acid methyl ester, 30-{(1-[galactos-1-yl]-1H-1,2,3-triazol-4-yl)-methoxy}-3β-hydroxylup-20(29)-en-28-oic acid methyl ester, 30-1H-1,2,3-triazol-4-yl-methylamino,30-oxolup-20(29)-en-3,28-diol diacetate, 30-(1-[peracetyl glucos-1-yl]-1H-1,2,3-triazol-4-yl)-methylamino,30-oxolup-20(29)-en-3,28-diol diacetate, 30-(1-[glucos-1-yl]-1H-1,2,3-triazol-4-yl)-methylamino,30-oxolup-20(29)-en-3,28-diol diacetate, 30-1H-1,2,3-triazol-4-yl-methylamino,30-oxolup-20(29)-en-3,28-diol, 30-(1-[peracetyl glucos-1-yl]-1H-1,2,3-triazol-4-yl)-methylamino,30-oxolup-20(29)-en-3,28-diol, 30-(1-[glucos-1-yl]-1H-1,2,3-triazol-4-yl)-methylamino,30-oxolup-20(29)-en-3,28-diol, 30-(1H-1,2,3-triazol-4-yl-methylamino)-3β-hydroxy,30-oxolup-20(29)-en-28-oic acid, 30-{(1-[peracetyl galactos-1-yl]-1H-1,2,3-triazol-4-yl)-methylamino}-3β-hydroxy,30-oxolup-20(29)-en-28-oic acid, 30-{(1-[galactos-1-yl]-1H-1,2,3-triazol-4-yl)-methylamino}-3β-hydroxy,30-oxolup-20(29)-en-28-oic acid, 30-(1H-1,2,3-triazol-4-yl-methylamino)-3β-hydroxy,30-oxolup-20(29)-en-28-oic acid methyl ester, 30-{(1-[peracetyl galactos-1-yl]-1H-1,2,3-triazol-4-yl)-methylamino}-3β-hydroxy,30-oxolup-20(29)-en-28-oic acid methyl ester, and 30-{(1-[galactos-1-yl]-1H-1,2,3-triazol-4-yl)-methylamino}-3β-hydroxy,30-oxolup-20(29)-en-28-oic acid methyl ester, in the form of optically active stereoisomers, racemates, or mixtures thereof, or in the form of pharmaceutically acceptable salts thereof.

* * * * *